US009198871B2

(12) United States Patent
Shlieout et al.

(10) Patent No.: US 9,198,871 B2
(45) Date of Patent: Dec. 1, 2015

(54) DELAYED RELEASE PANCREATIN COMPOSITIONS

(75) Inventors: George Shlieout, Sehnde (DE); Claus-Juergen Koelln, Neustadt (DE); Frithjof Sczesny, Hannover (DE); Jens Onken, Barsinghausen (DE); Andreas Koerner, Springe (DE)

(73) Assignee: Abbott Products GmbH, Hanover (DE)

( * ) Notice: Subject to any disclaimer, the term of this patent is extended or adjusted under 35 U.S.C. 154(b) by 1272 days.

(21) Appl. No.: 11/464,754

(22) Filed: Aug. 15, 2006

(65) Prior Publication Data
US 2007/0148153 A1 Jun. 28, 2007

Related U.S. Application Data

(60) Provisional application No. 60/708,526, filed on Aug. 15, 2005, provisional application No. 60/708,692, filed on Aug. 15, 2005.

(51) Int. Cl.
*A61K 9/50* (2006.01)
*A61K 9/16* (2006.01)
*A61K 38/54* (2006.01)
*A61K 38/46* (2006.01)
*A61K 38/47* (2006.01)
*A61K 38/48* (2006.01)

(52) U.S. Cl.
CPC .............. *A61K 9/50* (2013.01); *A61K 9/1635* (2013.01); *A61K 9/5036* (2013.01); *A61K 38/465* (2013.01); *A61K 38/47* (2013.01); *A61K 38/48* (2013.01); *A61K 38/54* (2013.01)

(58) Field of Classification Search
CPC ..... A61K 38/465; A61K 38/47; A61K 38/48; A61K 38/54; A61K 9/50
See application file for complete search history.

(56) References Cited

U.S. PATENT DOCUMENTS

| | | |
|---|---|---|
| 3,324,002 A | 6/1967 | Antonides |
| 3,803,305 A | 4/1974 | Thuillier |
| 3,950,508 A * | 4/1976 | Mony ................... A61K 9/2009 424/465 |
| 3,956,483 A | 5/1976 | Lewis |
| 3,986,927 A | 10/1976 | Melnick et al. |
| 3,991,180 A | 11/1976 | Boettner et al. |
| 4,019,958 A | 4/1977 | Hell et al. |
| 4,079,125 A | 3/1978 | Sipos |
| 4,106,991 A | 8/1978 | Markussen et al. |
| 4,242,219 A | 12/1980 | Bogerman et al. |
| 4,280,971 A | 7/1981 | Wischniewski et al. |
| 4,447,412 A | 5/1984 | Bilton |
| 4,490,361 A | 12/1984 | Heldebrant |
| 4,533,562 A | 8/1985 | Ikegami et al. |
| 4,623,624 A | 11/1986 | Schultze |
| 4,689,297 A | 8/1987 | Good et al. |
| 4,775,536 A * | 10/1988 | Patell ................... A61K 31/60 424/471 |
| 4,786,505 A | 11/1988 | Lovgren et al. |
| 4,929,774 A | 5/1990 | Fukamachi et al. |
| 5,068,110 A | 11/1991 | Fawzi et al. |
| 5,219,572 A | 6/1993 | Sivaramakrishnan et al. |
| 5,225,202 A | 7/1993 | Hodges et al. |
| 5,260,074 A | 11/1993 | Sipos |
| 5,300,433 A | 4/1994 | Hrinda et al. |
| 5,302,400 A | 4/1994 | Sipos |
| 5,324,649 A | 6/1994 | Arnold et al. |
| 5,374,657 A | 12/1994 | Kyle |
| 5,378,462 A * | 1/1995 | Boedecker ........... A61K 9/1641 424/408 |
| 5,489,530 A | 2/1996 | Braatz et al. |
| 5,536,661 A | 7/1996 | Boel et al. |
| 5,570,104 A | 10/1996 | Hayashi |
| 5,614,189 A | 3/1997 | Huge-Jensen |
| 5,618,710 A | 4/1997 | Navia et al. |
| 5,645,832 A | 7/1997 | Braatz et al. |
| 5,658,871 A | 8/1997 | Batenburg et al. |
| 5,719,115 A | 2/1998 | Paatz et al. |
| 5,725,880 A | 3/1998 | Hirakawa et al. |
| 5,750,104 A | 5/1998 | Sipos |
| 5,750,148 A | 5/1998 | Maruyama et al. |
| 5,766,912 A | 6/1998 | Boel et al. |
| 5,783,545 A | 7/1998 | Paatz et al. |
| 5,801,022 A | 9/1998 | Navia et al. |
| 5,849,296 A | 12/1998 | Navia et al. |
| 5,863,759 A | 1/1999 | Boel et al. |

(Continued)

FOREIGN PATENT DOCUMENTS

| | | |
|---|---|---|
| CA | 2263703 | 8/1999 |
| DE | 2035739 A1 | 1/1972 |

(Continued)

OTHER PUBLICATIONS

21 CFR 201.302 "Notice to manufacturers, packers, and distributors of drugs for internal use which contain mineral oil" (Apr. 2001).*

(Continued)

*Primary Examiner* — Brian-Yong Kwon
*Assistant Examiner* — Andrew S Rosenthal
(74) *Attorney, Agent, or Firm* — Lisa V. Mueller; Michael Best & Friedrich LLP

(57) ABSTRACT

An enteric-coated oral dosage form comprising an acid labile active pharmaceutical ingredient where the composition is substantially free of monomeric phthalic acid esters and synthetic oils is described herein. Also provided are methods for making and using the enteric-coated oral dosage form. The disclosed pharmaceutical compositions comprise an enteric coating which includes at least one plasticizer, at least one film-forming agent and optionally at least one anti-sticking agent.

32 Claims, No Drawings

(56) References Cited

U.S. PATENT DOCUMENTS

| | | | |
|---|---|---|---|
| 5,869,438 A | 2/1999 | Svendsen et al. | |
| 5,874,558 A | 2/1999 | Boel et al. | |
| 5,879,920 A | 3/1999 | Dale et al. | |
| 5,976,529 A | 11/1999 | Navia et al. | |
| 5,993,806 A | 11/1999 | Galle | |
| 6,004,768 A | 12/1999 | Navia et al. | |
| 6,011,001 A | 1/2000 | Navia et al. | |
| 6,025,391 A | 2/2000 | Haeberlin et al. | |
| 6,030,798 A | 2/2000 | Braatz et al. | |
| 6,051,220 A | 4/2000 | Scharpe | |
| 6,054,136 A | 4/2000 | Farah et al. | |
| 6,140,475 A | 10/2000 | Margolin et al. | |
| 6,187,572 B1 | 2/2001 | Platz et al. | |
| 6,224,910 B1 | 5/2001 | Ullah et al. | |
| 6,267,985 B1 | 7/2001 | Chen et al. | |
| 6,278,794 B1 | 8/2001 | Parekh et al. | |
| 6,312,704 B1 | 11/2001 | Farah et al. | |
| 6,348,442 B2 | 2/2002 | Markussen | |
| 6,355,461 B2 | 3/2002 | Henriksen et al. | |
| 6,426,091 B1 * | 7/2002 | Okumura | A61K 9/2081 424/464 |
| 6,692,771 B2 | 2/2004 | Pather et al. | |
| 6,734,188 B1 | 5/2004 | Rhodes et al. | |
| 6,749,851 B2 | 6/2004 | Mann et al. | |
| 6,767,729 B1 | 7/2004 | Nagano et al. | |
| 7,122,357 B2 | 10/2006 | Sander-Struckmeier et al. | |
| 7,211,281 B2 | 5/2007 | Van Beek et al. | |
| 7,479,378 B2 | 1/2009 | Potthoff et al. | |
| 7,658,918 B1 | 2/2010 | Ortenzi | |
| 8,221,747 B2 | 7/2012 | Ortenzi | |
| 8,246,950 B2 | 8/2012 | Ortenzi | |
| 2001/0046493 A1 | 11/2001 | Margolin et al. | |
| 2002/0061302 A1 | 5/2002 | Sander-Struckmeier et al. | |
| 2002/0137156 A1 | 9/2002 | Margolin et al. | |
| 2002/0146451 A1 | 10/2002 | Sharma et al. | |
| 2003/0007962 A1 | 1/2003 | Vergez et al. | |
| 2003/0017144 A1 | 1/2003 | Margolin et al. | |
| 2003/0021844 A1 | 1/2003 | Barthelemy et al. | |
| 2003/0049245 A1 | 3/2003 | Mann et al. | |
| 2003/0086948 A1 | 5/2003 | Benameur et al. | |
| 2003/0104048 A1 | 6/2003 | Patel et al. | |
| 2003/0175259 A1 | 9/2003 | Karageozian et al. | |
| 2003/0180352 A1 * | 9/2003 | Patel et al. | 424/465 |
| 2003/0211127 A1 | 11/2003 | Margolin et al. | |
| 2004/0013697 A1 | 1/2004 | Berndl et al. | |
| 2004/0033220 A1 | 2/2004 | Hartmann | |
| 2004/0057944 A1 | 3/2004 | Galle et al. | |
| 2004/0101562 A1 * | 5/2004 | Maio | 424/488 |
| 2004/0161423 A1 | 8/2004 | Kumar | |
| 2004/0202643 A1 | 10/2004 | Margolin et al. | |
| 2004/0213847 A1 | 10/2004 | Matharu et al. | |
| 2005/0250817 A1 | 11/2005 | Shlieout | |
| 2007/0148151 A1 | 6/2007 | Frink | |
| 2007/0148152 A1 * | 6/2007 | Shlieout et al. | 424/94.3 |
| 2007/0178120 A1 | 8/2007 | Morrison et al. | |
| 2008/0019959 A1 | 1/2008 | Becher et al. | |
| 2008/0292610 A1 | 11/2008 | Hartmann | |
| 2009/0130063 A1 | 5/2009 | Becher et al. | |
| 2009/0226414 A1 | 9/2009 | Tijssen et al. | |

FOREIGN PATENT DOCUMENTS

| | | |
|---|---|---|
| DE | 2410241 A1 | 9/1975 |
| DE | 2512746 A1 | 9/1976 |
| DE | 2626109 A1 | 12/1976 |
| DE | 2923279 C2 | 11/1980 |
| DE | 3642853 A1 | 6/1988 |
| DE | 4203315 A1 | 8/1992 |
| DE | 4200002 | 7/1993 |
| DE | 4322229 A1 | 1/1995 |
| DE | 4344215 A1 | 6/1995 |
| DE | 19907764 A1 | 11/1999 |
| DE | 19848849 A1 | 4/2000 |
| DE | 19856415 | 6/2000 |
| DE | 10012095 A1 | 9/2000 |
| DE | 29824797 U1 | 8/2002 |
| EP | 0008780 A2 | 3/1980 |
| EP | 0019253 A1 | 11/1980 |
| EP | 0021129 A2 | 1/1981 |
| EP | 0035780 | 9/1981 |
| EP | 0141607 A2 | 5/1985 |
| EP | 0170360 A1 | 2/1986 |
| EP | 0193829 A2 | 9/1986 |
| EP | 0206417 A2 | 12/1986 |
| EP | 0238023 | 9/1987 |
| EP | 0304331 A2 | 2/1989 |
| EP | 0304332 A2 | 2/1989 |
| EP | 0305216 | 3/1989 |
| EP | 0326026 B1 | 8/1989 |
| EP | 0458845 A1 | 8/1990 |
| EP | 0458849 A1 | 8/1990 |
| EP | 0407225 A1 | 1/1991 |
| EP | 0600868 A1 | 12/1991 |
| EP | 0550450 A1 | 2/1992 |
| EP | 0592478 A1 | 1/1993 |
| EP | 0583726 A2 | 2/1994 |
| EP | 0691982 B1 | 1/1996 |
| EP | 0828509 A1 | 12/1996 |
| EP | 0826375 B1 | 3/1998 |
| EP | 0973878 A1 | 10/1998 |
| EP | 0897985 A2 | 2/1999 |
| EP | 1010423 A2 | 6/2000 |
| EP | 1138333 B1 | 4/2001 |
| EP | 1186658 | 3/2002 |
| EP | 1261368 A2 | 12/2002 |
| EP | 1279402 A1 | 1/2003 |
| EP | 05107472 | 8/2005 |
| EP | 05107474 | 8/2005 |
| EP | 1593688 | 11/2005 |
| EP | 2278002 | 1/2011 |
| FR | 2313916 A1 | 1/1977 |
| GB | 1509866 | 5/1978 |
| JP | 04936885 A | 4/1974 |
| JP | 58148814 A | 9/1983 |
| JP | 58179492 | 10/1983 |
| JP | 59169491 A | 9/1984 |
| JP | 61162185 | 7/1986 |
| JP | 62-029950 | 2/1987 |
| JP | 04-023991 | 1/1992 |
| JP | 4187085 A | 7/1992 |
| JP | 8143457 A | 6/1996 |
| JP | 09125096 A | 5/1997 |
| WF | WO 2005/012911 | 2/2005 |
| WO | WO 82/03871 | 11/1982 |
| WO | 87/07292 A1 | 12/1987 |
| WO | 89/08694 A1 | 9/1989 |
| WO | 89/08695 A1 | 9/1989 |
| WO | 91/06638 A1 | 5/1991 |
| WO | 91/07948 | 6/1991 |
| WO | 91/14454 A1 | 10/1991 |
| WO | WO 91/16060 | 10/1991 |
| WO | WO 91/18623 | 12/1991 |
| WO | WO 92/02617 | 2/1992 |
| WO | 92/12645 A1 | 8/1992 |
| WO | 92/13030 A1 | 8/1992 |
| WO | WO 93/00924 | 1/1993 |
| WO | 93/07260 A1 | 4/1993 |
| WO | 93/07263 A1 | 4/1993 |
| WO | 93/18790 | 9/1993 |
| WO | WO 94/08603 | 4/1994 |
| WO | WO 95/07688 | 3/1995 |
| WO | WO 95/08983 | 4/1995 |
| WO | WO 95/15681 | 6/1995 |
| WO | 95/22625 A1 | 8/1995 |
| WO | 96/00343 A1 | 1/1996 |
| WO | 96/16151 A1 | 5/1996 |
| WO | 96/38170 A1 | 12/1996 |
| WO | 96/38527 A1 | 12/1996 |
| WO | 97/23605 A1 | 7/1997 |
| WO | 97/39116 A1 | 10/1997 |
| WO | WO 97/42980 | 11/1997 |
| WO | WO 98/00169 | 1/1998 |
| WO | WO 98/38292 | 9/1998 |

(56) References Cited

FOREIGN PATENT DOCUMENTS

| WO | WO 98/46732 | | 10/1998 |
|---|---|---|---|
| WO | WO 98/52561 | | 11/1998 |
| WO | WO 9920745 | A1 * | 4/1999 |
| WO | WO 99/28344 | | 6/1999 |
| WO | 99/44589 | A1 | 9/1999 |
| WO | 00/01793 | A1 | 1/2000 |
| WO | WO 00/34510 | | 6/2000 |
| WO | WO 00/54799 | | 9/2000 |
| WO | WO 01/01960 | | 1/2001 |
| WO | 01/25412 | A1 | 4/2001 |
| WO | 01/37808 | A1 | 5/2001 |
| WO | 01/58276 | A2 | 8/2001 |
| WO | WO 01/68139 | | 9/2001 |
| WO | 02/20746 | A1 | 3/2002 |
| WO | 02/28369 | A1 | 4/2002 |
| WO | 02/40045 | | 5/2002 |
| WO | WO 02/36156 | | 5/2002 |
| WO | 02/060474 | A2 | 8/2002 |
| WO | WO 03/047595 | | 6/2003 |
| WO | 03/055967 | A1 | 7/2003 |
| WO | 03/080827 | A2 | 10/2003 |
| WO | WO 2004/007707 | | 1/2004 |
| WO | 2004/069872 | A1 | 8/2004 |
| WO | 2005/070962 | A1 | 8/2005 |
| WO | WO 2005/092370 | | 10/2005 |
| WO | 2006/044529 | A1 | 4/2006 |
| WO | 2006/136159 | A2 | 12/2006 |
| WO | 2007/020260 | A2 | 2/2007 |
| WO | 2007020259 | | 2/2007 |
| WO | WO 2007/014896 | | 2/2007 |
| WO | WO 2007/135125 | | 11/2007 |
| WO | 2008/079685 | A2 | 7/2008 |

OTHER PUBLICATIONS

Porter, S.C. "Coating of Pharmacetuical Dosage Forms" Chapter 46. Remington: The Science and Practice of Pharmacy. Lippincott Williams & Wilkins: Philadelphia, 2005; 21st Edition; Chapter 46; pp. 929-938.*
"Gastric Juice" (http://www.thefreedictionary.com/gastric+juice) accessed Aug. 2, 2013.*
Porter, S. C."Coating of Pharmacetuical Dosage Forms" Chapter 46. Remington: The Science and Practice of Pharmacy. Lippincott Williams & Wilkins: Philadelphia, 2005; 21st Edition; Chapter 46; pp. 929-938.*
Directive 2003/36/EC of the European Parliament and of the Council of May 26, 2003, Official Journal of the European Union, p. L 156/26-30.
Turner et al., The Inactivation of Viruses in Pig Slurries: A Review, Bioresource Technology, vol. 61 (1997) p. 9-20.
Braeuniger et al., Further studies on thermal resistance of bovine parvovirus against moist and dry heat, Int. J. Hyg. Environ. Health, vol. 203 (2000) p. 71-75.
Committee for Proprietary Medicinal Products, Note for Guidance on Virus Validation Studies: The Design, Contribution and Interpretation of Studies Validating the Inactivation and Removal of Viruses, The European Agency for the Evaluation of Medicinal Products, Feb. 14, 1996, p. 1-13.
Thomson et al., Ch. 73 Porcine parvovirus infection, Infectious Diseases of Livestock vol. 2 (2nd ed. 2004) p. 806-814.
Guidance for Industry SUPAC-MR, Modified Release Solid Oral Dosage Forms, Sep. 1997, p. 1-36.
21 CFR 201.302 Notice to manufacturers, packers, and distributors of drugs for internal use which contain mineral oil, Apr. 2001.
International Search Report for PCT/EP2006/065311, Feb. 2, 2007.
Written Opinion of the International Searching Authority for PCT/EP2006/065311, Feb. 2, 2007.
Chemical Abstract, No. 99:200535j, "Capsules Containing Stable Digestive Enzymes", vol. 99, p. 342 (1983).
D'Costa, D., "Diabetic Neuropathic Cachexia Associated with Malabsorption," Diabetic Medicine, vol. 9/2, pp. 203-205 (1992).
Delhaye, M., "Comparative Evaluation of a High Lipase Pancreatic Enzyme Preparation and a Standard Pancreatic Supplement for Treating Exocrine Pancreatic Insufficiency in Chronic Pancreatitis," European Journal of Gastronenterology and Hepatology, vol. 8/7, pp. 699-703 (1996).
European Search Report for European Patent Application No. EP93112848 (Apr. 15, 1994).
European Search Report for European Patent Application No. EP 05733481.5 (Oct. 1, 2007).
Fiedler, Herbert P. (Lexikon der Hilfsstoffe fuer Pharmazie, Kosmetik and Angrenzende Gebiete, 5 Aufli. 2002), Encyclopedia of Excipients for Pharmaceuticals, Cosmetics and Related Areas, vol. 5, pp. 733 and 995, including English translation (cover page, pp. 747 & 921) (Total: Six (6) pages). Printed and bound by R. Oldenbourg Graphische Betriebe Druckerel GmbH, Kirchheim, Germany.
ICH Harmonised Tripartite Guideline, Table of Content and pp. 1-16 (1999).
International Preliminary Report of Patentability for PCT/EP2006/064717 (Oct. 11, 2007).
International Preliminary Report of Patentability for PCT/EP2006/065311 (Feb. 20, 2008).
International Preliminary Report of Patentability for PCT/EP2006/065313 (Feb. 20, 2008).
International Preliminary Report of Patentability for PCT/EP2007/054880 (Nov. 27, 2008).
International Search Report for PCT/EP2000/002261 (Jul. 11, 2000).
International Search Report and Written Opinion for PCT/EP2006/064717 (Nov. 20, 2006).
International Search Report and Written Opinion for PCT/EP2006/065313 (Feb. 2, 2007).
International Search Report and Written Opinion for PCT/EP2007/054880 (Oct. 2, 2007).
Nakamura, et al., Pancreas, vol. 16(3), pp. 329-336. (1998).
"Pancreatin", The American Heritage Dictionary of the English Language, 4th Edition Boston, Houghton Mifflin (2002). www.bartleby.com/61/ (printed Mar. 21, 2007).
"Pancreatin juice", The American Heritage Dictionary of the English Language, 4th Edition Boston, Houghton Mifflin (2002). www.bartleby.com/61/ (printed Mar. 21, 2007).
Simek, I., "Substitution Therapy in Insufficient External Pancreatic Secretion," Online Medline Databse (1993).
Subramanian et al., "Effect of lipid excipients on in vitro pancreatic lipase activity," Drug Dev. Ind. Pharm., vol. 29(8), pp. 885-890 (2003).
Tischer et al., "Replication of procine circovirus: induction by glucosamine and cell cycle dependence," Archives of Virology, vol. 96, pp. 39-57 (1987).
Ullman's Encyclopedia, pp. 179, 180 and 199 (1987).
Eurand S.A., Notice of Opposition againsts the European Patent No. EP 1931317., Sep. 23, 2009.
McGinity, Aqueous Polymeric Coatings for Pharmaceutical Dosage, Marcel Dekker, Inc.,1989.
Murthy, et al., "In Vitro Release Characteristics of Hard Shell Capsule Products Coated with Aqueous- and Organic-Based Enteric Polymers," Journal of Biomaterials Application, J. Biomater Appl., vol. 3, pp. 52-79 (1988), available at http://jba.sagepub.com.
Nordmark Arzneimittel GmbH & Co. KG, Notice of Opposition against the European Patent No. EP 1931317., Aug. 6, 2009 with translation.
Oshima, et al., "Preparation of Rapidly Disintegrating Tablets Containing Itraconazole Solids Dispersion," Chem. Pharm. Bull., vol. 55(11), pp. 1557-1562 (2007).
Reynolds, "A New Technique for the Production of Spherical Particles," Manufact. Chemist & Aerosol News, pp. 40-43 (Jun. 1970).
Sucker et al., "Pharmazeutische Techologie," pp. 273-283 (1991) with translation.
USP 32, NF 27, "Pancrelipase Delayed-Release Capsules." (2009).
Hogan et al., Pharmaceutical Coating Technology, Chapter 14, pp. 409-439 (1995).
Kirk-Othmer, Encyclopedia of Chemical Technology, 3rd ed., vol. 23, pp. 724-725 (1984).
Pharmaceutic Excipients, 5th ed., Cetyl Alcohol, pp. 155-156 (2006).

(56) References Cited

OTHER PUBLICATIONS

Remington, The Science and Practice of Pharmacy, 20th ed, pp. 326 and 1035-1036 (2000).
Sun et al., "Fuidized-bed spray coated porus hydrogel beads for sustained release of diclofenac sodium" Journal of Controlled Relase, vol. 47, pp. 247-260 (1997).
Thoma et al., "Influence of aqueous coatings on the stability of enteric coated pellets and tablets," European Journal of Pharmaceutics and Biopharmaceutics, vol. 47, pp. 39-50 (1999).
Wan et al "Plasticizers and their effects on microencapsulation process by spay-dryng in an aqueous sysem" J. Microencapsulation, vol. 9(1), pp. 53-62 (1992).
2.9.1 Disintegration of Tablets and Capsules, European Pharmacopoeia 5.3, pp. 3351-3353 (2006).
Archibald, A.L., "Comparison of the Serum Amylases of Farm Animals," Comp. Biochem. Physiol., vol. 88B (3), pp. 963-968 (1987).
Aquacoat ECD—FMC Biopolymer—Bulletin AECD-30-05/18/97. RS (1997).
Carriere, et al., "Quantitative Study of Disgestive Enzyme Secretion and Gastrointestinal Lipolysis in Chronic Pancreatitis," Clinical Gastroenterology and Hepatology, vol. 3(1), pp. 28-38 (2005).
Chueshov, et al., Industrial Technology of Drugs and Medicine, vol. 2, NFAU Publishing House, pp. 359-363 (2002) [with Translation].
Cunningham, L., "Reactivation of Diethyl p-Nitrophenyl Phosphate-Inhibited α-Chymotrypsin by Hydroxylamine," Journal of Biological Chemistry, vol. 207, pp. 443-458 (1954).
De Fiebre et al. "Elimination of Salmonellae from Animal Glandular Products," Applied Microbiology, vol. 17(3), pp. 344-346 (1969).
Delchier, et al., "Fate of Orally Ingested Enzymes in Pancreatic Insufficiency: Comparison of Two Pancreatic Enzyme Preparations," Aliment. Pharmacol. Therap., vol. 5, pp. 365-378 (1991).
Dimagno, et al., "Fate of Orally Ingested Enzymes in Pancreatic Insufficiency," The New England Journal of Medicine, vol. 296(23), pp. 1318-1322 (1977).
Dutta, et al., "Critical Examination of Therapeutic Efficacy of a pH-Sensitive Enteric-Coated Pancreatic Enzyme Preparation in Treatment of Exocrine Pancreatic Insufficiency Secondary to Cystic Fibrosis," Digestive Diseases and Sciences, vol. 33(10), pp. 1237-1244 (1988).
Enzyme Nomenclature., Recommendations of the Nomenclature Committee of the International Union of Biochemistry and Molecular Biology on the Nomenclature and Classification of Enzymes by the Reactions they Catalyse, available at http://www.chem.qmul.ac.uk/iubmb/enzyme/.
English Abstract of JP 4187085.
Estes, et al., "Proteolytic Enhancement of Rotavirus Infectivity: Molecular Mechanisms," Journal of Virology, vol. 39(3), pp. 879-88 (1981).
European Patent Appl. No. 06778012.2 Office Action dated Dec. 7, 2010 (5 pages).
Fang, et al., "Purification and Characterization of Adult Diarrhea Rotavirus: Identification of Viral Structural Proteins," Journal of Virology, vol. 63(5), pp. 2191-2197 (1989).
Federal Register, vol. 69(82), Part IV, Apr. 28, 2004.
Fiedler, Herbert P. Encyclopedia of Excipients for Pharmaceuticals, Cosmetics and Related Areas, 5th ed., pp. 1284-1287 (2002).
Gregory, P.C., "Gastrointestinal pH, Motility/Transit and Permeability in Cystic Fibrosis," J Pediatr Gastroenterol Nutr, vol. 23(5), pp. 513-523 (1996).
Guarner, et al., "Fate of Oral Enzymes in Pancreatic Insufficiency," Gut, vol. 34, pp. 708-712 (1993).
International Preliminary Report of Patentability for PCT/EP2008/065586 (May 18, 2010).
International Search Report for PCT/EP2008/065586 (Dec. 19, 2008).
International Search Report PCT/EP2009/050010 (May 7, 2009).
Jiang et al., "Biochemical Characterization of the Structural and Nonstructural Polypeptides of a Porcine Group C Rotavirus," Journal of Virology, vol. 64(7), pp. 3171-3178 (1990).
Keller, et al., "Pancreatic Enzyme Supplementation Therpay," Current Treatment Option in Gastroenterology, vol. 6, pp. 369-374 (2003).
Keller, et al., "Human Pancreatic Exocrine Response to Nutrients in Health and Disease," Gut, vol. 54(Suppl. VI), pp. vi1-vi28 (2005).
Kobayashi, et al., "Susceptibility of Heptitis B Virus to Disinfectants or Heat," Journal of Clinical Microbiology, vol. 20(2), pp. 214-216 (1984).
Korzhavykh, et al., "Tablets and Their Various Forms", Russian Pharmacies, No. 19, pp. 1-5 (2010) [with Translation].
Kreon® 25000 (magnified photograph).
Kreon® 25000 Gebrauchsinformation (2007), English Translation.
Layer, et al., "Fate of Pancreatic Enzymes During Small Intestinal Aboral Transit in Humans," The American Physiology Society, pp. G475-G480 (1986).
Layer, et al., "Pancreatic Enzymes in Chronic Pancreatitis," International Journal of Pancreatology, Col. 15(1), pp. 1-11 (1994).
Maunula, L., "Molecular Epidemiology of Human Rotaviruses—A Study in Genetic Diversity," Academic Dissertation, Haartman Institute, pp. 1-116, Helsinki 2001.
Material Safety Data Sheet, Pancreatin 4X USP (10X), Invitrogen Corp., pp. 1-7 (Rev. Apr. 16, 2005).
Michen, et al., "Isoelectric Points of Viruses," Journal of Applied Microbiology, vol. 109, pp. 388-397 (2010).
Naftifine HCI MSDS (Jun. 23, 2004), available at http://pharmacycide.com/msds/Naftifine_HCL.
Nilsson, et al., "Biosynthesis and morphogenesis of group C rotavirus in swine testicular cells," Arch. Virol., vol. 133, pp. 21-37 (1993).
Notice of Opposition filed of EP1931316.
Notices of Opposition Filed by Nordmark Arzneimittel GmbH & Co. Kg and Eurand S.p.A, EP 1931317; Reply of the Patent Proprietor to the Notice of Opposition.
Register of Pharmaceuticals in Russia, RP-Pharmacist, Annual Collection, Issue 5, p. 772 (2003) [with Translation].
Sachs-Barrable, et al., "Lipid Excipients Peceol and Gelucire 44/14 Decrease P-Glycoprotein Mediated Efflux of Rhodamine 123 Partially Due to Modifying P-Glycoprotein Protein Expression within Caco-2 Cells," J Pharm Pharmaceut Sci, vol. 10(3), pp. 319-331 (2007).
Saif et al., "Serial Propagation of Porcine Group C Rotavirus (Pararotavirus) in a Continuous Cell Line and Characterization of the Passaged Virus," Journal of Clinical Microbiology, vol. 26(7), pp. 1277-1282 (1988).
Sanekata, et al., "Isolation of Group B Porcine Rotavirus in Cell Culture," Journal of Clinical Microbiology, vol. 34(3), pp. 759-761 (1996).
Savage et al., "Determination of Adequate Moisture Content for Efficient Dry-Heat Viral Inactivation in Lyophilized Factor VIII Loss on Drying and by Near Infrared Spectroscopy," Biologicals, vol. 26, pp. 119-124 (1998).
Sofer, et al., "Part 6, Inactivation Methods Grouped by Virus," BioPharm Internationals, S-37-42 (2003).
The Ministry of Health, Labour and Welfare Ministerial Notification No. 285, Japan Pharmacopoeia, 8 pages (2006).
Tsunemitsu, et al., "Isolation, Characterization, and Serial Propagation of a Bovine Group C Rotavirus in a Monkey Kidney cell Line (MA104)," Journal of Clinical Microbiology, vol. 29(11), pp. 2609-13 (1991).
U.S. Appl. No. 11/464,704, filed Aug. 15, 2006, Aug. 21, 2009 Non-Final Office Action.
U.S. Appl. No. 11/464,704, filed Aug. 15, 2006, Feb. 19, 2010 Response to the Aug. 21, 2009 Non-Final Office Action.
U.S. Appl. No. 11/464,704, filed Aug. 15, 2006, May 26, 2010 Final Office Action.
U.S. Appl. No. 11/464,704, filed Aug. 15, 2006, Nov. 24, 2010 Response to the May 26, 2010 Final Office Action.
United States Pharmacopoeia for Pancrelipase Delayed-Release Capsules (2 pages) (2006).
United States Pharmacopoeia Method 711 Dissolution (18 pages) (2006).
Walsh, et al., "Tryosinogen and Chymotrypsinogen as Homologous Proteins," PNAS, vol. 52, pp. 884-889 (1964).

(56) References Cited

OTHER PUBLICATIONS

Wallis, et al., "Plaque Enhancement of Enteroviruses by Magnesium Chloride, Cysteine, and Pancreatin," Journal of Bacteriology, vol. 91(5), pp. 1932-1935 (1996).
Watkins, Paul, "The Barrier Function of CYP3A4 and P-Glycoprotein in the Small Bowel," Advanced Drug Delivery Reviews, vol. 27, pp. 161-170 (1997).
Worthington Enzyme Manual, Lipase, (1993), pp. available at http://www.worthington-biochem.com/PL/default.html (2 pages).
Worthington Enzyme Manual, Trypsin (1993), available at http://www.worthington-biochem.com/TRY/default.html (3 pages).
Worthington Enzyme Manual, Trypsinogen (1993), available at http://www.worthington-biochem.com/TG/default.html (1 page).
Benzonana, et al., "Etude Cinetique de L'Action de la Lipase Pancreatique Sur Des Triglycerides en Emulsion Essai D'Une Enzymologie en Milieu Heterogene," Biochimica Et Biophysica ACTA, 105:121-136 (1965) (English Abstract).
Bezzine, et al., "Human Pancreatic Lipase: Colipase Dependence and Interfacial Binding of Lid Domain Mutants," Biochemistry, 23:5499-5510 (1999).
Borgstrom, et al., "Pancreatic Juice Co-Lipase: Physiological Importance," Biochimica Et Biophysica ACTA, 242:509-513 (1971).
Borgstrom, et al., "Pancreatic Lipase and Colipase: Interaction and Effect of Bile Salts and Other Detergents," Eur. J. Biochem, 37:60-68 (1973).
Borgstrom, "Binding of Pancreatic Colipase to Interfaces; Effects of Detergents," FEBS Letters, 71(2):201-204 (1976).
Borgstrom, "On the Interactions Between Pancreatic Lipase and Colipase and the Substrate and the Importance of Bile Salts," Journal of Lipid Research, 16:411-417 (1975).
EP 1931317, Aptalis Pharma S.r.L, Submission of Opponent 02 in Preparation of Oral Proceedings, Aug. 3, 2011.
EP 1931317, Nordmark Arzneimittel GmbH & Co. KG, Submission of Opponent 01 in Preparation of Oral Proceedings, Jul. 20, 2011 (with Translation).
Gargouri, et al., "Studies on the Detergent Inhibition of Pancreatic Lipase Activity," Journal of Lipid Research, 24:1336-1342 (1983).
Saunders, et al., "Lecithin Inhibits Fatty Acid and Bile Salt Absorption from Rat Small Intestine In Vivo," Lipids, 11 (12):830-832 (1976).
Ammon, et al., "Effect of Lecithin on Jejunal Absorption of Micellar Lipids in Man and on Their Monomer Activity in vitro," Lipds, 14(4):395-400 (1978).
Jones, et al., "Effects of Exogenous Emulsifiers and Fat Sources on Nutrient Digestibility, Serum Lipids, and Growth Performance in Weanling Pigs," J. Anim Sci., 70:3473-3482 (1992).
Kammlott, et al., "Experiments to Optimize Enzyme Substitution Therapy in Pancreatic Duct-Ligated Pigs," Journal of Animal Physiology and Animal Nutrition, 89:105-108 (2005).
Lukovac, et al., "Gelucire 44/14 Improves Fat Absorption in Rats with Impaired Lipolysis," Biochimica et Biophysica Acta, 1801:665-673 (2010).
O'Doherty, et al., "Role of Luminal Lecithin in Intestinal Fat Absorption," Lipids, 8(5):249-255 (1972).
Overland, et al., "Lecithin in Swine Diets: I. Weanling Pigs," J. Anim Sci, 71:1187-1193 (1993).
Overland, et al., "Effect of Lecithin on the Apparent Ileal and Overall Digestibility of Crude Fat and Fatty Acids in Pigs," J. Anim Sci, 72:2022-2028 (1994).
Tabeling, et al., "Studies on Nutrient Digestibilities (Pre-Caecal and Total) in Pancreatic duct-Ligated Pigs and the Effects of Enzyme Substitution," J. Anim. Physiol. A. Anim. Nutr., 82:251-263 (1999).
Copending U.S. Appl. No. 14/074,255, filed Nov. 7, 2013.
Brewer et al., "Porcine encephalomyocarditis virus persists in pig myocardium and infects human myocardial cells," J. Virology (2001) 75(23):11621-11629.
McLean et al., "Contamination detection in animal cell culture," Encyclopedia of Cell Technology (2000) 1-2:586-598.
U.S. Appl. No. 11/460,330 dated Oct. 18, 2013 (22 pages).
U.S. Appl. No. 11/751,497 dated Oct. 21, 2013 (13 pages).
Axcan Pharma, Inc., Viokase Prescribing Information, Mar. 2000, 3 pages.
Bieger, W. et al., "Two-dimensional isoelectric focusing/sodium dodecyl sulfate gel electrophoresis of protein mixtures containing active or potentially active proteases analysis of human exocrine pancreatic proteins," Anal. Biochem. (1980) 109:222-230.
Challapalli, K.K. et al., "High reproducibility of large-get two-dimensional electrophoresis," Electrophoresis (2004) 25:3040-3047.
Cunningham, N. et al., "Replication of avian infectious bronchitis virus in African green monkey kidney cell line Vero," J. Gen. Virol. (1972) 16:423-427.
DeRobertis, Cell & Mol. Biol. (1980) 7th Ed., 132-133.
Definition of "picornaviridae," http://medical-dictionary.thefreedictionary.com/Picornaviridae, downloaded Jul. 26, 2011.
Dony, J. et al., "Etide electrophoretique et immunoelectrophoretique de preparations enzymatiques injectables: preparation d'origine pancreatique et preparations d'origine testiculaire," progress in Immunological Standardization (1970) 4:395-405, with English translation.
Fallis, LS. et al., "Observations on some metabolic changes after total pancreatoduodenectomy," Annals of Surgery (1948) 639-667.
Goerg, A et al., "The current state of two-dimensional electrophoresis with immobilized gH gradients," Electrophoresis (2000) 21:1037-1053.
Goldman, D. et al., "Human lymphocyte polymorphisms detected by quantitative two-dimensional electrophoresis," Am. J. Hum. Genet. (1983) 35:827-837.
Goodman & Gilman's "The Pharmacological Basis of Therapeutics," 8th Edition, Pergamon Press (1990) 1471-1477.
Jenkins, L.W. et al., "Conventional and functional proteomics using large formal two-dimensional gel electrophoresis 24 hours after controlled cortical impact in postnatal day 17 rats," J. Neurotrauma (2002) 19(6):715-740.
Klotz, H.P., "Lyophilized pancreatic extract, an aid in the treatment of mild diabetes," La Nouvelle Presse Medicals (1975) 4(32):2333, abstract.
Korneeva, O.S. et al., "Identification of catalytically active groups of wheat (Triticum aestivum) germ lipase," Appl. Biochem. & Microbiol. (2008) 44(4):349-355.
Lebowitz, J. et al., "Modern analytical ultracentrifugation in protein science: a tutorial review," Protein Sci. (2002) 11:2067-2079.
Marumerizer QJ-1000T Spheronizer (http://www.lcicorp.com/industrial_granulation/detail/category/marumerizer_qj1000 (accessed Jul. 26, 2013).
May et al., J. Biol. Standardization (1982) 10:249-259.
Meyer, Boyd Anal. Chem. (1959) 31:215-219.
Murlin et al., "The influence of alkili upon the glycos uria, hyperglycemia and carbon dioxide combining power in human diabetes," Proceedings of the Society for Experimental Biol. Med. (1917) 14:8-9.
Nishihara, J.C. et al., "Quantitative evaluation of proteins in one- and two-dimensional polyacrylamide gels using a fluorescent stain," Electrophoresis (2002) 23:2203-2215.
Padfield, P.J. et al., "The use of two-dimensional gel electrophoresis and high-performance liquid chromatography for the analysis of pancreatic juice," The Pancreas: Biology, Pathbiology, and Disease, Second Edition, Chapter 14 (1993) 265-273.
Pariza, M.W. et al., "Evaluating the safety of microbial enzyme preparations used in food processing: update for a new century," Regul. Toxicol. Pharmacol. (2001) 33(2):173-186.
Reed, L.J. et al., "A simple method of estimating fifty percent end points," Amer J. of Hygiene (1938) 27(3):493-497.
Ridder, G. et al., "Quantitative analysis of pattern recognition of two-dimensaional electrophoresis gels," Clin. Chem. (1984) 30(12):1919-1924.
Scharpe, S. et al., "Isoelectric characterization of porcine pancreative alpha amylases," Journal De Pharmacie De Belgique (1973) 28(6):705-708.
Scheele, G.A., "Two-dimensional gel analysis of soluble proteins," J. Biol. Chem. (1975) 250(14):5375-5385.
Shimura, K. et al., "Affinophoresis in two-dimensional agarose gel electrophoresis specific separation of biomolecules by a moving affinity ligand," Anal. Biochem. (1987) 161(1):200-206.

(56) References Cited

OTHER PUBLICATIONS

Smolka, M. et al., "Quantitative protein profiling using two-dimensional gel electrophoresis, isotope-coded affinity tag labeling, and mass spectrometry," Mol. Cell Proteomics (2002) 1.1:19-29.
Spearman, C., "The method of 'right and wrong cases' ('constant stimuli') without Gauss's formulae," Brit. J. Psych. (1908) vol. II, Part 3, 227-242.
Van Den Bergh, G. et al., "Fluorescent two-dimensional difference gel electrophoresis and mass spectrometry identify age-related protein expression differences for the primary visual cortex of kitten and adult cat," J. Neurochem. (2003) 85:193-205.
Veronese et al., "Photo inactivation of enzymes by linear and angular furocoumarins," Photochem & Photobiol. (1982) 36(1):25-30.
Villegas et al., "A rapid method to produce high yields of purified rotavirus particles," J. Virol. Meth. (2002) 104:9-19.
Voss, T. et al., "Observations on the reproducibility and matching efficiency of two-dimensional electrophoresis gels: consequences for comprehensive data analysis," Electrophoresis (2000) 21:3345-3350.
European Patent Office Search Report and Opinion for Application No. 07120740.1 dated Mar. 1, 2008.
European Patent Office Search Report for Application No. 10178590 dated Dec. 9, 2010.
European Patent Office Search Report and Preliminary Opinion for Application No. 06114329 dated Aug. 1, 2006.
European Search Report for Application No. 07120740.1 dated Mar. 3, 2008.
European Search Report for Application No. 97114330 dated Jun. 5, 2002.
International Preliminary Report on Patentability for Application No. PCT/EP2004/008332 dated Jan. 30, 2006.
International Search Report and Written Opinion for Application No. PCT/EP2005/051295 dated Jun. 24, 2005.
International Search Report for Application No. PCT/EP2004/008332 dated Nov. 24, 2004.
International Search Report for Application No. PCT/EP2007/054880 dated Sep. 18, 2007.
Written Opinion for Application No. PCT/EP2007/054880 dated Sep. 18, 2007.
U.S. Appl. No. 11/085,073 dated Oct. 23, 2006 (12 pages).
U.S. Appl. No. 11/085,073 dated Jul. 13, 2007 (13 pages).
U.S. Appl. No. 11/085,073 dated Apr. 7, 2008 (17 pages).
U.S. Appl. No. 11/085,073 dated Feb. 26, 2010 (19 pages).
U.S. Appl. No. 11/460,330 dated Nov. 12, 2010 (13 pages).
U.S. Appl. No. 11/460,330 dated Aug. 4, 2011 (21 pages).
U.S. Appl. No. 11/460,330 dated Apr. 9, 2012 (21 pages).
U.S. Appl. No. 11/464,704 dated May 26, 2010.
U.S. Appl. No. 11/464,704 dated Aug. 2, 2013 (21 pages).
U.S. Appl. No. 11/751,497 dated Nov. 12, 2009 (12 pages).
U.S. Appl. No. 11/751,497 dated Jul. 14, 2010.
U.S. Appl. No. 11/751,497 dated Mar. 10, 2011 (8 pages).
U.S. Appl. No. 11/751,497 dated Apr. 17, 2013 (16 pages).
U.S. Appl. No. 12/271,480 dated Nov. 3, 2010.
U.S. Appl. No. 12/271,480 dated Jul. 14, 2011 (12 pages).
U.S. Appl. No. 12/271,480 dated May 24, 2013 (14 pages).
U.S. Appl. No. 12/271,480 dated Sep. 19, 2013 (13 pages).
Notice of Allowance for U.S. Appl. No. 11/085,073 dated Apr. 1, 2014 (17 pages).
Office Action for U.S. Appl. No. 11/460,330 dated Jun. 2, 2014 (23 pages).
Office Action for U.S. Appl. No. 11/464,704 dated Apr. 25, 2014 (25 pages).
U.S. Appl. No. 60/708,526 by George Shlieout et al., filed Aug. 15, 2005.
Biswal, S. et al, "Production variables affecting characteristics of pellets in melt pellitization with wax combination in a laboratory scale spheronizer," Acta Pharm. (2009) 59:199-210.
Loa, C.C. et al., "Purification of turkey coronavirus by stephacryl size-exclusion chromatography," J. Virol. Meth. (2002) 104:187-194.

Mesiha, M.S. et al., "A screening study of lubricants in wet powder masses suitable for extrusion-spheronization," Drug Dev. & Ind. Pharm. (1993) 19(8):943-959.
PEG 4000, EM Grade, Technical Data Sheet 279, Polysciences, Inc. (1999) 2 pages.
ShinEtsu Chemical Company, USP Hypromellose Phthalate Enteric Coating Material (Sep. 2002) 10 pages.
Tabasi, S.H. et al., "Quality by design, Part I: Application of NIR spectroscopy to monitor tablet manufacturing process," J. Pharm. Sci. (2008) 97:4040-4051.
Tabasi, S.H. et al., "Quality by design, Part II: Application of NIR spectroscopy to monitor the coating process for a pharmaceutical sustained release product," J. Pharm. Sci. (2008) 97:4052-4066.
Tabasi, S.H. et al., "Quality by design, Part III: Study of curing process of sustained release coated products using NIR spectroscopy," J. Pharm. Sci. (2008) 97:4067-4086.
Ueba, O., "Respiratory synctial virus. I. Concentration and purification of the infectious virus," Acta Medica Okayama (1978) Article 2, 32(4):265-272.
U.S. Pharmacopeia 28, National Formulary 23, 23rd Edition, (2004) 10 pages.
U.S. Appl. No. 12/271,480 dated Jan. 6, 2015 (15 pages).
Aptalis Farma S.r.L., Certificate of Inscription in the Regular Identification Data of the Company (Jul. 15, 2011) 4 pages.
Decision to Revoke the European Patent No. EP1931317 in the Opposition filed by Nordmark against European Patent No. 1931317 dated Nov. 17, 2011.
Die Tablette, Handbuch der Entwicklung, Herstellung and Qualitatssicherung, Editiv cantor Verlag Aulendorf (2002) Seiten 85-89, 91-106, 583,584, W.A. Ritschel eds.
Grounds of Appeal in the Opposition filed by Aptalis Pharma S.r.L. against European Patent No. 1931316 dated Jan. 2, 2013.
Grounds of Appeal in the Opposition filed by Nordmark against European Patent No. 1931317 dated Mar. 15, 2012.
Pharmazeutische Technologie, Georg Thieme Verlag Stuttgart (1978/1991) 2:178-179.
Reply from Opponent in the Opposition filed by Nordmark against European Patent No. 1931317 dated Jul. 20, 2012.
Reply of Proprietor in the Opposition filed by Aptalis Pharma S.r.L. against European Patent No. 1931316 dated Jun. 7, 2011.
Reply to Appeal in the Opposition filed by Nordmark Against European Patent No. 1931317 dated Sep. 28, 2012.
Reply to Appeal in the Opposition filed by Aptalis Pharma S.r.L. against European Patent No. 1931316 dated May 13, 2013.
Reply to Summons to Attend Oral Proceedings: filing of new main claim request in the Opposition filed by Aptalis Pharma S.r.L. against European Patent No. 1931316 dated Feb. 23, 2012.
Reply to Summons to Attend Oral Proceedings: New Written Submissions and Claim Amendments in the Opposition filed by Nordmark against European Patent No. 1931317 dated Aug. 4, 2011.
Results and Minutes of Oral Proceedings in the Opposition filed by Aptalis Pharma S.r.L. against European Patent No. 1931316 dated Sep. 5, 2012.
Results and Minutes of Oral Proceedings in the Opposition filed by Nordmark against European Patent No. 1931317 dated Oct. 6, 2011.
Rompp Chemie Lexikon, Jurgen Falbe et al. editors, (1992) Georg Thieme Verlag, 9:3532 "Polyethylenglykole".
Summons to Oral Proceedings in the Opposition filed by Aptalis Pharma S.r.L. against European Patent No. 1931316 dated Dec. 22, 2011.
Summons to Oral Proceedings in the Opposition filed by Nordmark Arzneimittel GmbH against European Patent No. 1931317 dated Mar. 29, 2011.
Technical Reports on Comparative Exp.x, examples Jan. 7 thru Jul. 7 (2009), including B810586 "PEG4000 iprop high"; B810587 "PEG2000"; B810588 "PEG8000"; B810589 "HPMC iprop equ"; B810590 "PVP iprop equ"; B810591 "HPMC iprop high"; and B810592 "PVP iprop low".
Written Submission in the Opposition filed by Nordmark against European Patent No. 1931317 dated Aug. 25, 2011.
Written Submission by Aptalis Pharma S.r.L. in the Opposition filed by Aptalis Pharma S.r.L. against European Patent No. 1931316 dated Mar. 12, 2012.

(56) References Cited

OTHER PUBLICATIONS

Written Submission by Opponent in the Opposition filed by Aptalis Pharma S.r.L. against European Patent No. 1931316 dated May 4, 2012.

United States Patent Office Action for U.S. Appl. No. 11/460,330 dated Jun. 5, 2015 (38 pages).

United States Patent Office Action for U.S. Appl. No. 11//751,497 dated May 22, 2015 (12 pages).

United States Patent Office Notice of Allowance for U.S. Appl. No. 12/271,480 dated Jul. 20, 2015 (13 pages).

United States Patent Office Action for U.S. Appl. No. 11/464,704 dated Jul. 28, 2015 (26 pages).

\* cited by examiner

DELAYED RELEASE PANCREATIN COMPOSITIONS

CROSS-REFERENCE TO RELATED APPLICATIONS

This application claims the benefit of U.S. Provisional Application Nos. 60/708,526 and 60/708,692 which were both filed Aug. 15, 2005 and are both hereby incorporated by reference.

FIELD OF THE INVENTION

Described herein is a pharmaceutical composition in an oral dosage form and methods for making and using the same. More specifically, described herein are pharmaceutical compositions for acid-labile active pharmaceutical ingredients in an enteric-coated oral dosage form where the dosage form is substantially free of both monomeric phthalic acid ester plasticizers and synthetic oils.

BACKGROUND

Numerous active pharmaceutical ingredients (API) are know to be incompatible with the acidic environment present in mammalian, such as human, stomachs. Due to this incompatibility, it can be advantageous to protect these acid-labile compounds until such time as they reach a point in the GI tract having a pH which is more compatible with the particular API. Controlled or delayed release pharmaceutical compositions for acid-labile drugs, in particular for acid-labile drugs that need to be delivered to the upper intestine of a mammal and where exposure of the acid-labile API to the acidic gastric environment is to be avoided, is often desirable.

One such acid-labile API which is advantageously delivered to the human duodenum is pancreatin. Pancreatin is a substance which is derived from mammalian pancreas glands and comprises different digestive enzymes such as lipases, amylases and proteases. Pancreatin has been used to treat pancreatic exocrine insufficiency (PEI) which is often associated with cystic fibrosis, chronic pancreatitis, post-pancreatectomy, post-gastrointestinal bypass surgery (e.g. Billroth II gastroenterostomy) and ductal obstruction from neoplasm (e.g. of the pancreas or common bile duct). Pancreatin microspheres are the treatment of choice for diseases or disorders caused by digestive enzyme deficiency in mammals such as humans. This is due to the fact that high-performance pancreatin microsphere products like Creon™ provide a therapeutically effective load of active enzymes while at the same time providing properly sized microspheres capable of targeting the optimal location in the digestive tract where digestive enzyme activity will be needed, in particular the upper intestine such as the duodenum.

Recently, governmental health authorities have initiated a reassessment of the compatibility of certain pharmaceutical excipients which had previously been used in the formulation of pancreatin-containing products and have provided advice concerning the use of specific pharmaceutical excipients such as mineral oil (see e.g. US Code of Federal Regulations, 21 CFR §201.302) and dibutyl phthalate (see e.g. directive 2003/36/EC of the European Parliament and the Council of 26 May 2003 amending for the 25$^{th}$ time Council Directive 76/769/EEC). As a result, it is now recommended that mineral oil not be provided indiscriminately to either pregnant women or infants. Similarly, health authorities today recommend restricting the use of dibutyl phthalate. Therefore, a need exists to provide patients with formulations of pharmaceutical products which would be responsive to the current advice of health authorities.

Some controlled release pharmaceutical preparations and/or methods for preparing them are disclosed in EP 0063014 or U.S. Pat. No. 5,725,880.

Pharmaceutical preparations which may comprise pancreatin and an enteric coating are disclosed in DE 19907764; EP 0021129 (U.S. Pat. No. 4,280,971); EP 0035780; EP 0583726 (U.S. Pat. No. 5,378,462); U.S. Pat. No. 5,225,202; U.S. Pat. No. 5,750,148; U.S. Pat. No. 6,224,910; US 2002/0146451 and WO 02/40045.

U.S. Pat. No. 4,786,505 discloses pharmaceutical preparations for oral use.

Published patent application US 2004/0213847 discloses delayed release pharmaceutical compositions containing proton pump inhibitors.

Published patent application US 2002/061302 discloses the use of physiologically acceptable enzyme mixtures for the treatment of diabetes.

SUMMARY

Accordingly, one embodiment disclosed herein is an enteric-coated oral dosage form containing an acid-labile API where the dosage form is substantially free of monomeric phthalic acid ester plasticizers and synthetic oils.

Other objects, features and advantages will be set forth in the Detailed Description that follows, and in part will be apparent from the description or may be learned by practice of the claimed invention. These objects and advantages will be realized and attained by the processes and compositions particularly pointed out in the written description and claims hereof.

DETAILED DESCRIPTION

While the present invention is capable of being embodied in various forms, the description below of several embodiments is made with the understanding that the present disclosure is to be considered as an exemplification of the invention, and is not intended to limit the disclosure to the specific embodiments and examples illustrated. The headings used throughout this disclosure are provided for convenience only and are not to be construed to limit the disclosure in any way. Embodiments illustrated under any heading may be combined with embodiments illustrated under the same or any other heading.

It has now been surprisingly discovered that a controlled release pharmaceutical composition comprising acid-labile drugs, such as pancreatin, in the upper intestine can be achieved by providing an enteric-coated oral dosage form wherein the enteric-coating comprises at least one plasticizer and at least one film-forming agent as described in more detail below. The new enteric coating as disclosed herein is substantially free of both, monomeric phthalic acid ester plasticizers, such as dibutyl phthalate, and synthetic oils, such as paraffins or mineral oils, while at the same time providing the desired targeted release and storage stability. The enteric coating as disclosed herein further provides beneficial properties which are comparable to the respective properties of pharmaceutical compositions which contains dibutyl phthalate and synthetic oil in the formulation.

It is therefore provided herein an enteric coating comprising
 a) one or more film-forming agents;
 b) at least one plasticizer in an amount of greater than about 1.5% by weight relative to the one or more film-forming agents wherein the plasticizer is substantially free of monomeric phthalic acid esters; and
 c) optionally at least one anti-sticking agent.

The enteric coating can be applied to oral dosage forms of acid-labile drugs, such as pancreatin, which need to be delivered to the GI tract at a location having a pH higher than the stomach. By applying the enteric coating as disclosed herein to oral dosage forms of acid-labile drugs, controlled release pharmaceutical compositions (CRPC) of the acid-labile drugs can be achieved.

Film-forming agent(s), plasticizer(s) and anti-sticking agent(s) (when present) as used for preparing the enteric coating are hereinafter commonly referred to as "non-solvent coating constituents".

Suitable film-forming agents include agar, Carbopol™ (carbomer) polymers (i.e. high molecular weight, crosslinked, acrylic acid-based polymers), carboxymethyl cellulose, carboxymethylethyl cellulose, carrageen, cellulose acetate phthalate, cellulose acetate succinate, cellulose acetate trimelliate, chitin, corn protein extract, ethyl cellulose, gum arabic, hydroxypropyl cellulose, hydroxypropylmethyl acetate succinate, hydroxypropyl methylcellulose acetate succinate, hydroxypropyl methylcellulose phthalate, methacrylic acid-ethyl methacrylate-copolymer, methyl cellulose, pectin, polyvinyl acetate phthalate, polivinyl alcohol, shellac, sodium alginate, starch acetate phthalate and/or styrene/maleic acid copolymer or mixtures of said film-forming polymers. Cellulose acetate phthalate, hydroxypropyl methylcellulose acetate succinate and/or methacrylic acid-ethyl methacrylate-copolymer are the preferred film-forming agents. Most preferred is hydroxypropyl methylcellulose phthalate, e.g. HP 55 or HPMCP HP-50. Synthetic oils are not to be regarded as preferred film-forming agents. The foregoing list of film-forming agents is not meant to be exhaustive but merely illustrative, as a person or ordinary skill in the art would understand that many other film-forming agents or combination of film-forming agents could also be used.

The plasticizer(s) may generally be present in an amount greater than about 1.5%, and typically in an amount between about 2% and about 20% by weight, relative to the film-forming agent. The plasticizer may contain saturated linear monohydric alcohols having 12 to 30 carbon atoms. More specifically, acceptable plasticizers include lauryl alcohol, tridecyl alcohol, myristyl alcohol, pentadecyl alcohol, cetyl alcohol, heptadecyl alcohol, stearyl alcohol, nonadecyl alcohol, arachic alcohol, behenyl alcohol, carnaubyl alcohol, ceryl alcohol, corianyl alcohol, melissyl alcohol, acetyl tributyl citrate, dibutyl sebacate, fatty acid esters of glycerol, glycerol, polyethylene glycol, propyleneglycol, sorbitan fatty acids, triacetin, triethyl citrate and mixtures of said plasticizers. Preferred plasticizers are cetyl alcohol, stearyl alcohol, triethyl citrate and mixtures thereof. When cetyl alcohol is used as a single plasticizer, it may be present in an amount of greater than about 1.5%, typically in an amount of about 2% to about 15%, preferably about 2% to about 10%, by weight relative to the film-forming agent. When triethyl citrate is used as a single plasticizer, it may be present in an amount between about 5% and about 20%, preferably between about 12% and about 15%, by weight relative to the film-forming agent. Synthetic oils and monomeric phthalic acid esters are not to be regarded as suitable plasticizers. The foregoing list of plasticizers is not meant to be exhaustive but merely illustrative, as a person or ordinary skill in the art would understand that many other plasticizers or combination of plasticizers could also be used so long as they are substantially free of both synthetic oils and monomeric phthalic acid esters.

In one embodiment the plasticizer is comprised of cetyl alcohol and triethyl citrate which are collectively present in an amount of greater than about 3%, typically in an amount of about 4% to about 20%, in particular between about 6% and about 15%, more particularly between about 7% and about 10%, by weight in relation to the film-forming agent. The weight to weight ratio of cetyl alcohol to triethyl citrate when both are present may be from about 0.05:1 to about 1:1, for example 0.1:1, 0.2:1, 0.3:1, 0.4:1, 0.5:1, 0.6:1, 0.7:1, 0.8:1 or 0.9:1. In particular, the ratio of cetyl alcohol to triethyl citrate may be from about 0.25:1 to about 0.5:1, preferably from about 0.3:1 to about 0.45:1, more preferably from about 0.35:1 to about 0.4:1, and even more preferably from about 0.38:1 to about 0.4:1 (w/w).

The enteric coating optionally comprises an anti-sticking agent. Suitable anti-sticking agents include dimethicone and castor oil. Dimethicone, in particular dimethicone 1000, is the preferred anti-sticking agent. The amount of anti-sticking agent (if present) in the enteric coating is between about 1.5% and about 3% by weight relative to the film-forming agent. Synthetic oils are not to be regarded as preferred anti-sticking agents. The foregoing list of anti-sticking agents is not meant to be exhaustive but merely illustrative, as a person or ordinary skill in the art would understand that many other anti-sticking agents or combination of anti-sticking agents could also be used.

Additional embodiments are also located in U.S. patent application Ser. No. 11/464,704 filed on Aug. 15, 2006 and claiming the benefit of U.S. Provisional Application Nos. 60/708,526 and 60/708,692 which were both filed on Aug. 15, 2005. U.S. patent application Ser. No. 11/464,704 is hereby incorporated by reference.

The term "synthetic oils" means unsaponifiable hydrocarbons or mixtures of hydrocarbons and comprises e.g. liquid and solid paraffins, in particular liquid paraffins (mineral oils), more particularly highly liquid paraffin (light mineral oil).

The phrase "substantially free of synthetic oils" means that the manufacturing processes described herein and used to make the enteric coating or the enteric coated oral dosage forms of acid-labile drugs where applicable do not utilize one or more synthetic oils as an excipient although synthetic oils may be present as pharmaceutically acceptable trace contaminants in the API, binding agent(s), enteric coating constituents, organic solvents and/or excipients which are used to manufacture the enteric coating and/or the enteric coated oral dosage forms of acid-labile drugs described herein.

The phrase "substantially free of monomeric phthalic acid esters" means that the manufacturing processes described herein and used to make the enteric coating or the enteric coated oral dosage forms of acid-labile drugs where applicable do not utilize one or more monomeric phthalic acid esters (e.g. dibutyl phthalate) as an excipient although monomeric phthalic acid esters may be present as pharmaceutically acceptable trace contaminants in the API, binding agent(s), enteric coating constituents, organic solvents and/or excipients which are used to manufacture the enteric coating and/or the enteric coated oral dosage forms of acid-labile drugs described herein.

Examples of acid-labile drugs which may be coated with the eneric coating as disclosed herein are e.g. (+)-N-{3-[3-(4-fluorophenoxy)phenyl]-2-cyclopenten-1-yl}-N-hydroxyurea, amylase, aureomycin, bacitracin, beta carotene, cephalosporins, chloromycetin, cimetidine, cisapride, cladribine, clorazepate, deramciclane, didanosine, digitalis glycosides, dihydrostreptomycin, erythromycin, etoposide, famotidine, hormones (in particular estrogens, insulin, adrenalin and heparin), lipase, milameline, novobiocin, pancreatin, penicillin salts, polymyxin, pravastatin, progabide, protease, quinapril, quinoxaline-2-carboxylic acid, [4-(R)-carbamoyl-1-(S-3-fluorobenzyl-2-(S),7-dihydroxy-7-methyloctyl]amide, quinoxaline-2-carboxylic acid[1-benzyl-4-(4,4-difluoro-I-hydroxy-cyclohexyl)-2-hydroxy-4-hydroxycarbamoyl-butyl]-amide, ranitidine, streptomycin, subtilin, sulphanilamide and acid-labile proton pump inhibitors like esomeprazole, lansoprazole, minoprazole, omeprazole, pantoprazole or rabeprazole. Amylase, lipase and protease may be coated together or separately. Amylases, lipases and proteases which are suitable as digestive enzyme supplement or digestive enzyme substitute in mammals, particularly humans, are preferred. Amylase, lipase and/or protease may be derived from microbial or animal, in particular mammalian, sources. Pancreatin is the preferred acid-labile drug. The foregoing list of acid-labile drugs is not meant to be exhaustive, but merely illustrative as a person of ordinary skill in the art would understand that many other acid-labile drugs or combination of acid-labile drugs could also be used.

Pancreatin is a mixture of different physiologically active endogenous ingredients which is derived from mammalian pancreas glands and comprises as its main constituents different digestive enzymes like lipases, amylases and proteases. Mammalian pancreatic lipase is typically used as a digestive enzyme supplement or substitute for the treatment of PEI but pancreatic proteases and amylases also contribute to the therapeutic value of pancreatin. Pancreatin for pharmaceutical use is typically of bovine or porcine origin. Porcine pancreatin is preferred.

The oral dosage form containing the acid-labile drugs may be in the form of, for example, capsules, granules, granulates, micropellets, microspheres, microtablets, pellets, pills, powders and/or tablets. For the purposes of this invention, the prefix "micro" is used to describe an oral dosage form if the diameter of the oral dosage form or all of its dimensions (length, height, width) is equal to or below about 5 mm.

In one embodiment the enteric coating comprises between about 20% and about 30% by weight, more preferably between about 22% and about 26% by weight, yet more preferably between about 22.5% and about 25% by weight of the total composition of the enteric coated oral dosage form or CRPC.

In one embodiment, the oral dosage form is a pancreatin micropellet or pancreatin microsphere which comprise between about 10% and about 95% by weight of pancreatin, between about 5% and about 90% by weight of at least one pharmaceutically acceptable binding agent and between 0% and about 10% by weight of at least one pharmaceutically acceptable excipient. More specifically, pancreatin micropellet cores can be produced by the process described herein which comprise between about 70% and about 90% by weight of pancreatin, between about 10% and about 30% by weight of at least one pharmaceutically acceptable binding agent and between 0% and about 5% by weight of at least one pharmaceutically acceptable excipient. In one embodiment, pancreatin micropellet cores can be produced which comprise between about 70% and about 90% by weight pancreatin, and between about 10% and about 30% by weight of at least one pharmaceutically acceptable binding agent. In one embodiment the pancreatin micropellet or pancreatin microsphere is approximately spherical and has a diameter between about 0.5 mm and about 2.0 mm.

Examples of pharmaceutically acceptable binding agents include polyethylene glycol 1500, polyethylene glycol 2000, polyethylene glycol 3000, polyethylene glycol 4000, polyethylene glycol 6000, polyethylene glycol 8000, polyethylene glycol 10000, hydroxypropyl methylcellulose, polyoxyethylen, copolymers of polyoxyethylen-polyoxypropylen and mixtures of said organic polymers. The foregoing list of pharmaceutically acceptable binding agents is not meant to be exhaustive, but merely illustrative as a person of ordinary skill in the art would understand that many other pharmaceutically acceptable binding agents or combination of binding agents could also be used. Polyethylene glycol 4000 is the preferred pharmaceutically acceptable binding agent.

Examples of suitable pharmaceutically acceptable excipients include gliding agents like magnesium stearate or calcium stearate, stearic acid, talcum and/or starch; fillers like calcium phosphate, corn starch, dextrans, dextrin, hydrated silicon dioxide, microcrystalline cellulose, kaolin, lactose, mannitol, polyvinyl pyrrolidone, precipitated calcium carbonate, sorbitol and/or talcum; disintegrating agents like Aerosil™ (silicic acid), alginic acid, amylose, calcium alginate, calcium carbonate, formaldehyde gelatin, pectic carbonate, sago starch, sodium bicarbonate and/or starch; and/or moisturizers like glycerol and/or starch. The foregoing list of pharmaceutically acceptable excipients is not meant to be exhaustive, but merely illustrative as a person or ordinary skill in the art would understand that many other pharmaceutically acceptable excipients or combination of excipients could also be used. For the purposes of the present disclosure, synthetic oils and monomeric phthalic acid esters are not to be regarded as suitable pharmaceutically acceptable excipients. In one embodiment, the pancreatin micropellets or pancreatrin microspheres contain no pharmaceutically acceptable excipients, but can optionally contain a greater amount of pancreatin.

In one embodiment, pancreatin micropellets can be prepared by a manufacturing process comprising the steps of:
  a) preparing an extrudable mixture comprising:
    i. about 10% to about 95% pancreatin;
    ii. about 5% to about 90% of at least one pharmaceutically acceptable binding agent;
    iii. 0% to about 10% of at least one pharmaceutically acceptable excipient; and
    iv. one or more enzyme-friendly organic solvents in an amount sufficient to form an extrudable mixture; wherein the percentages of components are weight to weight of the pancreatin micropellets;
  b) creating pancreatin micropellets from the extrudable mixture;
  c) forming the pancreatin micropellets into approximately spherical or approximately ellipsoidal shape in the presence of additional enzyme-friendly organic solvent; and
  d) removing the one or more enzyme-friendly organic solvents from the pancreatin micropellets such that the pancreatin micropellets are substantially free of the one or more enzyme-friendly organic solvents.

Process variations wherein the pancreatin micropellets are substantially free of synthetic oils are preferred.

Further, process variations wherein the pharmaceutically acceptable excipients are present in an amount of 0% are preferred.

The amounts of pancreatin, pharmaceutically acceptable binding agent(s), pharmaceutically acceptable excipient(s) and/or enzyme-friendly organic solvent may be varied by those skilled in the art to arrive at the pancreatin micropellets having the preferred composition and characteristics as indicated herein.

Enzyme-friendly organic solvents facilitate mixing and other processing procedures and may afterwards be removed, for example, by drying. Typically, after removal of the enzyme-friendly organic solvents, a certain amount of solvent remains in the pancreatin micropellet cores. The remaining solvent in the micropellet cores can comprise enzyme-friendly organic solvents, water, or a mixture of enzyme-friendly organic solvents with water. If water is present as a solvent, this will typically have been present in the pancreatin which was used as the starting material. The amount of solvent present in the pancreatin micropellet cores after removal of the enzyme-friendly organic solvents is typically less than about 5% and normally less than about 3% by weight of the pancreatin micropellet core.

Examples of suitable enzyme-friendly organic solvents are acetone, chloroform, dichloromethane or straight-chained or branched $C_{1-4}$-alcohols, particularly methanol, ethanol, 1-propanol, 2-propanol, 2-butanol, tert-butanol or mixtures of said solvents. 2-propanol is the preferred enzyme-friendly organic solvent. For the purposes of the present disclosure, synthetic oils are not to be regarded as suitable enzyme-friendly organic solvents. The enzyme-friendly organic solvent is typically used in an amount of about 15% to about 35% by weight, preferably of about 20% to about 30% by weight, relative to the amount of pancreatin used. The foregoing list of suitable enzyme-friendly organic solvents is not meant to be exhaustive, but merely illustrative as a person or ordinary skill in the art would understand that many other enzyme-friendly organic solvents or combination of solvents could also be used. The amounts of pancreatin, pharmaceutically acceptable binding agent(s), pharmaceutically acceptable excipient(s) and/or enzyme-friendly organic solvent may be varied by those skilled in the art to arrive at the pancreatin micropellets having the preferred composition as indicated herein.

The term "substantially free of enzyme-friendly organic solvents" means that the quantity of enzyme-friendly organic solvents present in the oral dosage form would be less than about 5% by weight.

Removal of the one or more enzyme-friendly organic solvents from the oral dosage form means that the oral dosage form is subject to conditions whereby it becomes substantially free from enzyme-friendly organic solvents. Removal of the enzyme-friendly organic solvents can be by methods known to those of ordinary skill in the art. The preferred method is by drying. Additionally, removal of the one or more enzyme-friendly organic solvents would also typically result in the oral dosage form containing an amount of water which is less than about 5% and typically less than about 3% by weight.

In one embodiment the pancreatin micropellets are created in process step b) by extrusion. Remarkably, an extrudable mixture is obtained even when the mixture is substantially free of synthetic oils. In process step b), if the creating of the micropellets from the extrudable mixture is accomplished by means of extrusion, then the temperature preferably does not exceed about 70° C. during extrusion, more preferably the temperature does not exceed about 50° C. Also, in the event of extrusion, piercing dies are preferably used which have a hole diameter of about 0.5 to about 2.0 mm, preferably of about 0.7 to about 1.5 mm, and more preferably about 0.8 mm. Preferably, the pancreatin micropellet or pancreatin microsphere has a diameter of about 0.5 to about 2.0 mm, in particular of about 0.7 to about 1.5 mm, 0.8 mm. If the extrudable mixture is extruded, then the extrudate fragments are brought to a suitable length for the forming step. This can be done e.g. by means of a cutting device arranged downstream to the extruding press in a manner known to the a person of ordinary skill in the art. The forming in process step c) can be carried out e.g. in a customary rounding apparatus. In the rounding apparatus, the extrudate fragments are then formed into an approximately spherical or approximately ellipsoidal shape in the presence of additional enzyme-friendly organic solvent which may be the same or different than the enzyme-friendly organic solvent used in process step a).

When prepared substantially free of synthetic oils, processing of the extrudate fragments in the rounding apparatus is improved relative to other known processes which use synthetic oils. For example, a lower amount of enzyme-friendly organic solvent needs to be added when forming the pancreatin micropellets into an approximately spherical or approximately ellipsoidal shape and fewer of the extrudate fragments stick to parts of the rounding apparatus when the process is practiced with an extruder and rounding apparatus.

The invention further provides a process for producing a CRPC which is an enteric coated oral dosage form of an acid-labile drug comprising the steps of:
  a. providing an oral dosage form of an acid-labile drug;
  b. providing an enteric-coating solution comprising
    i. one or more film-forming agents;
    ii. at least one plasticizer in an amount of greater than about 1.5% by weight relative to the one or more film-forming agents wherein the plasticizer is substantially free of monomeric phthalic acid esters;
    iii. optionally, at least one anti-sticking agent; and
    iv. one or more volatile organic solvents;
  c. coating the oral dosage form with the enteric-coating solution wherein the product temperature of the pancreatin micropellet cores during coating is kept at a temperature suitable to apply the enteric-coating solution;
  d. drying the coated oral dosage form.

In the foregoing process for producing an enteric-coated oral dosage form of an acid-labile drug, the oral dosage form(s), the film-forming agent(s), the plasticizer(s), the anti-sticking agent(s) and the enzyme-friendly organic solvents generally have the meanings as set forth above.

Process step b) may be performed at a temperature between about 15° C. and about 60° C. Performing process step b) at ambient temperature (i.e. room temperature, approximately between about 20° C. and about 30° C.), is preferred. Examples of suitable enzyme-friendly organic solvents include acetone, 2-butanol, tert.-butanol, chloroform, dichloromethane, ethanol, methanol, 1-propanol, 2-propanol and mixtures of said solvents. Acetone, ethanol and 2-propanol or their mixtures are preferred as enzyme-friendly organic solvents. Acetone is most preferred. The foregoing list of enzyme-friendly organic solvents in process step b) is not meant to be exhaustive but merely illustrative, as a person or ordinary skill in the art would understand that many other enzyme-friendly organic solvents or combination of solvents could also be used.

The enzyme-friendly organic solvent is typically used in an amount between about 6 and about 10 times, preferably between about 7 and about 8 times, the weight of the non-solvent coating constituents used to prepare the pancreatin micropellets. For example, if the non-solvent coating constituents make up to a total weight of about 1.5 g, then about 9 g to about 15 g of enzyme-friendly organic solvent may be used in process step a).

The enteric coating optionally comprises an anti-sticking agent. Suitable anti-sticking agents include dimethicone and castor oil. Dimethicone, in particular dimethicone 1000, is the preferred anti-sticking agent. The anti-sticking agent is usually present in the enteric coating in an amount of between about 1.5% and about 3% by weight relative to the film-forming agent. Synthetic oils are not to be regarded as preferred anti-sticking agents. The foregoing list of anti-sticking agents is not meant to be exhaustive but merely illustrative, as a person or ordinary skill in the art would understand that many other anti-sticking agents or combination of anti-sticking agents could also be used.

Due to the process for producing CRPCs, viz. the coating process as described herein, pharmaceutically acceptable residual amounts of the enzyme-friendly organic solvent(s) present in the enteric-coating solution may still be present in the final enteric coated oral dosage form. It is understood that CRPCs comprising pharmaceutically acceptable residual amounts of enzyme-friendly organic solvent(s) are within the scope of the present invention.

In process step c) the product temperature of the oral dosage form, in one embodiment, is usually maintained between about 30° C. and about 60° C. while coating, preferably between about 32° C. and about 55° C., more preferred between about 35° C. and about 50° C., most preferably between about 37° C. and about 49° C. In process step c), when cetyl alcohol or both cetyl alcohol and triethyl citrate are used the product temperature of the oral dosage form is maintained between about 40° C. and about 46° C. Maintaining the product temperature of the oral dosage form within the preferred temperature ranges while coating results in improved gastric-acid resistant properties of the CPRC, in particular when the enteric coating comprise cetyl alcohol and triethyl citrate as plasticizers. The coating in process step c) can be accomplished by any process or method known to a person of ordinary skill in the art. Spray coating is preferred. If the coating in process step c) is performed by spray coating, the spray rate can be between about 97 kg/h and about 115 kg/h. Usually, process step c) is performed in a way that the enteric coating comprises between about 20% and about 30% by weight, preferably between about 22% and about 26% by weight and more preferably between about 22.5% and about 25% by weight of the total composition of the enteric coated oral dosage form or CRPC. The exact parameters to be applied in process step c) to achieve the desired enteric coating will depend on the coating technique used. The person skilled in the art understands how to achieve coating films of a desired thickness when using different coating techniques.

Drying of the enteric-coated oral dosage form of the acid-labile drug in process step dd.) is preferably performed between about 30° C. and about 90° C., preferably between about 30° C. and about 55° C., and preferably between about 35° C. and about 50° C. for a period of between about 1 hour and about 60 hours, between about 6 hours and about 60 hours, preferably for a period of between about 6 hours and about 36 hours.

In one embodiment of the process for producing an enteric coated oral dosage form of an acid-labile drug, the acid-labile drug is pancreatin. Disclosed herein is a process for the manufacture of pancreatin micropellets, comprising the steps of:
aa. providing pancreatin micropellet cores wherein the pancreatin micropellet cores are substantially free of synthetic oils;
bb. providing an enteric-coating solution comprising
  i. one or more film-forming agents;
  ii. a plasticizer in an amount greater than about 1.5% by weight relative to the one or more film-forming agents film-forming agents wherein the plasticizer is substantially free of monomeric phthalic acid esters; and
  iii. optionally, at least one anti-sticking agent, and
  iv. one or more enzyme-friendly organic solvent(s);
cc. coating the pancreatin micropellet cores with the enteric-coating solution wherein the temperature of the pancreatin micropellet cores during coating is kept at a temperature suitable for applying the enteric-coating solution; and
dd. drying the coated pancreatin micropellet cores.

In the foregoing process for producing pancreatin micropellets, the film-forming agent(s), the plasticizer(s), the anti-sticking agent(s) and the enzyme-friendly organic solvents generally have the meanings as previously set forth.

Due to the process for producing pancreatin micropellets, viz. the coating process as described herein, pharmaceutically acceptable residual amounts of the enzyme-friendly organic solvent(s) present in the enteric-coating solution may still be present in the pancreatin micropellet after drying. It is understood that pancreatin micropellets comprising pharmaceutically acceptable residual amounts of enzyme-friendly organic solvent(s) are within the scope of the present invention.

Process step bb) may be performed at a temperature between about 15° C. and about 60° C. Performing process step bb) at ambient temperature (i.e. room temperature, approximately between about 20° C. and about 30° C.), is preferred. Examples of suitable enzyme-friendly organic solvents include acetone, 2-butanol, tert.-butanol, chloroform, dichloromethane, ethanol, methanol, 1-propanol, 2-propanol and mixtures of said solvents. Acetone, ethanol and 2-propanol or their mixtures are preferred as enzyme-friendly organic solvents. Acetone is most preferred. The foregoing list of enzyme-friendly organic solvents in process step bb.) is not meant to be exhaustive but merely illustrative, as a person or ordinary skill in the art would understand that many other enzyme-friendly organic solvents or combination of solvents could also be used.

The enzyme-friendly organic solvent is typically used in an amount between about 6 and about 10 times, preferably between about 7 and about 8 times, the weight of the non-solvent coating constituents used to prepare the pancreatin micropellets. For example, if the non-solvent coating constituents make up to a total weight of about 1.5 g, then about 9 g to about 15 g of enzyme-friendly organic solvent may be used in process step aa).

In process step cc.) the temperature of the pancreatin micropellet core, in one embodiment, is usually maintained between about 30° C. and about 60° C. while coating, preferably between about 32° C. and about 55° C., more preferred between about 35° C. and about 50° C., most preferably between about 37° C. and about 49° C. In process step cc.), when cetyl alcohol or both cetyl alcohol and triethyl citrate are used the temperature of the pancreatin micropellet core is maintained between about 40° C. and about 46° C. Maintaining the temperature of the pancreatin micropellet cores within the preferred temperature ranges while coating results in improved gastric-acid resistant properties of the pancreatin micropellets, in particular when the enteric coating comprise cetyl alcohol and triethyl citrate as plasticizers. The coating in process step cc.) can be accomplished by any process or method known to a person of ordinary skill in the art. Spray coating is preferred. Usually, process step cc.) is performed in a way that the enteric coating comprises between about 20% and about 30% by weight, preferably between about 22% and about 26% by weight and more preferably between about 22.5% and about 25% by weight of the total composition of the pancreatin micropellet. The exact parameters to be applied in process step cc.) to achieve the desired enteric coating will depend on the coating technique used. The person skilled in the art understands how to achieve coating films of a desired thickness when using different coating techniques.

Drying of the enteric-coated pancreatin micropellet cores in process step dd) is performed between about 30° C. and about 90° C. preferably between about 30° C. and about 55° C., preferably between about 35° C. and about 50° C., and for a period of between about 1 hour and about 60 hours, between about 6 hours and about 60 hours, preferably for a period of between about 6 hours and about 36 hours.

The invention further provides a CRPC which is an enteric coated oral dosage form of an acid-labile drug, in particular of pancreatin, which is obtainable by the process or its variants described herein. If the CRPC is a pancreatin micropellet or pancreatin microsphere, the preferred a diameter is about 0.6 to about 2.1 mm and preferrably between about 0.7 mm and 1.6 mm.

In one embodiment, oral CRPCs are described wherein pancreatin is the acid-labile drug for delivery to an area of the GI tract having a pH greater than the pH of the stomach, specifically to the small intestine, usually to the duodenum, of mammals such as humans. The oral CRPCs comprising pancreatin are particularly suited for the prophylaxis and/or treatment of digestive disorders of different origins like maldigestion and/or for the prophylaxis and/or treatment of pancreatitis, cystic fibrosis, diabetes type 1, diabetes type 11 and/or other conditions resulting from pancreatine exocrine insufficiency in mammals and humans.

Maldigestion in mammals such as humans is usually based on a deficiency of digestive enzymes, in particular on a deficiency of endogenous lipase, but also of protease and/or amylase. The cause of such a deficiency of digestive enzymes is frequently a hypofunction of the pancreas (e.g. pancreatic insufficiency, usually known as pancreatic exocrine insufficiency), the organ which produces the largest quantity of, and the most important, endogenous digestive enzymes. If the pancreatic insufficiency is pathological, it may be congenital or acquired. Acquired chronic pancreatic insufficiency may, for example, result from alcoholism. Congenital pancreatic insufficiency may, for example, result from disease such as cystic fibrosis. The consequences of the deficiency of digestive enzymes may be severe symptoms of under-nutrition and malnutrition, which may be accompanied by increased susceptibility to secondary illnesses. In one specific embodiment, pancreatin micropellets according to the invention are therefore particularly suited for treating pancreatic exocrine insufficiency of any origin.

In another embodiment, an enteric coated oral dosage form of pancreatin is provided as previously described, for the manufacture of a medicament for the treatment of medical conditions such as digestive disorders, pancreatic exocrine insufficiency, pancreatitis, cystic fibrosis, diabetes type I and/or diabetes type II.

In yet another embodiment, a method is provided for the treatment of a medical condition such as digestive disorders, pancreatic exocrine insufficiency, pancreatitis, cystic fibrosis, diabetes type I and/or diabetes type II by administering a therapeutically effective amount of an enteric coated oral dosage form of pancreatin to a person in need of such treatment.

The CRPCs described herein comprise enteric coated capsules, granules, granulates, micropellets, microspheres, microtablets, pellets, pills, powders and/or tablets. Enteric coated granules, granulates, micropellets, microspheres, pellets, pills or powders, if desired may be filled into capsules or sachets or may be compressed to form microtablets or tablets. Equally, uncoated granules, granulates, micropellets, microspheres, pellets, pills or powders may be first compressed to form microtablets or tablets which may then be coated with the enteric coating as provided according to the invention. Microtablets or tablets may likewise be filled into capsules. Capsules or sachets maybe opened to permit mixing of the contents with compatible foods or liquids to facilitate administration of the contents of the capsule or sachet.

Granules are asymmetric agglomerates of powder particles cemented together and having no regular geometric form. The surface of the granule may be spherical, rod-shaped or cylindrical and is usually uneven and ridged. Granules are preferably produced by melt or wet granulation. Granulates are usually defined to be sedimented agglomerates of granules. Tablets are usually made from the powder or the granules. Pellets and micropellets can be produced either by exploiting the thermoplastic properties of the excipients in a high share mixer (melt pelletisation) or by other methods such as extrusion (e.g. melt extrusion or wet extrusion) and spheronisation. Pharmaceutical pellets are usually of a defined geometrical form and have a generally smooth surface. Specific methods of producing micropellets or microspheres are described herein. Microspheres and micropellets are the preferred oral dosage forms described herein.

The enteric coating as disclosed herein will usually be applied to oral dosage forms selected from granules, granulates, micropellets, microspheres, microtablets, pellets, pills, powders and/or tablets and the coated oral dosage forms may then be incorporated into uncoated capsules. However, in an alternative embodiment, the invention also comprises enteric coated capsules which contain coated or, more commonly, uncoated oral dosage forms selected from granules, granulates, micropellets, microspheres, microtablets, pellets, pills, powders and/or tablets. The coated oral dosage forms of the acid-labile drug selected from granules, granulates, micropellets, microspheres, microtablets, pellets, pills, powders and/ or tablets or the capsules may further be incorporated into at least one outer package e.g. selected from blisters or bottles. In embodiments of the invention, a pharmaceutical pack or kit is provided comprising one or more containers filled with the ingredients of a pharmaceutical composition of the invention. Associated with such container(s) can be various written materials such as instructions for use, or a notice in the form prescribed by a governmental agency regulating the manufacture, use or sale of pharmaceuticals products, which notice reflects approval by the agency of manufacture, use, or sale for human or veterinary administration.

The CRPCs as disclosed herein are substantially free of both monomeric phthalic acid ester plasticizers, such as dibutyl phthalate, and synthetic oils, such as paraffins or mineral oils, while providing the desired performance in terms of targeted release and storage stability. Further, the CRPCs presently disclosed, in particular in their preferred embodiments, possess superior gastric acid resistance and protective properties, e.g. superior resistance and protective properties in an acidic environment, specifically at pH 1 and/or pH 5. The enteric coating as proposed for the presently disclosed CPRCs have additional desirable properties such as dissolution profiles. In prefered CRPCs disclosed herein, the plasticizer is comprised of cetyl alcohol and triethyl citrate (CA/ TEC-Compositions). CA/TEC-Compositions in general preserve a higher lipase content when pancreatin is the acid-labile drug and usually possess a lower water content compared to CRPCs when other plasticizers are used.

EXAMPLES

The following examples are meant to be illustrative and not to limit the present disclosure. Other suitable modifications and adaptations are of the variety normally encountered by those skilled in the art and are fully within the spirit and scope of the present disclosure.

A. Preparation of an Enteric Coated Oral Dosage Form of an Acid-Labile Drug

1. Preparation of Uncoated Pancreatin Micropellets 15.9 kg of pancreatin was mixed with 3.975 kg of polyethylene glycol 4000 in a commercially available high shear mixer and thoroughly moistened with 3.975 kg of 2-propanol. The resulting mixture was extruded by means of a commercially available extruding press which was equipped with a piercing die having 0.8 mm internal diameter bores and a cutting device arranged downstream. The temperature was less than 50° C. while pressing. The extruded mass was cut into extrudate fragments of approximately 5 mm length by means of the cutting device.

The resulting 14.64 kg of the extrudate fragments were transferred in four portions of roughly equal size to a commercially available rounding apparatus and rounded to give approximately elliptically or approximately spherically shaped micropellet cores. An additional 135 g of 2-propanol was added while rounding.

After drying in a commercially available continuous vacuum dryer (Vötsch type) at a temperature in a range from between 35° C. and 50° C. for 12 hours, the pancreatin micropellets were graded, first with a 3.15 mm sieve (sieving of oversize grain >3.15 mm) and then with a 0.7 mm sieve (sieving of undersize grain <0.7 mm) and afterwards with a 1.25 mm sieve (sieving of oversize grain >1.25 mm) to yield 11.98 kg of pancreatin micropellet cores having a pancreatin content of 80% and a bulk density of 0.67 g/ml.

2. Enteric Coating of Pancreatin Micropellet Cores

A coating solution was prepared by adding 1623.2 g of hydroxypropyl methylcellulose phthalate (HP 55), 90.2 g of triethyl citrate, 34.3 g of cetyl alcohol and 38.9 g of dimethicone 1000 to 14030 g of acetone at room temperature while stirring.

5025 g of pancreatin micropellet cores (prepared analogously to the process as described herein) were fed into a commercially available fluid bed coater and were spray-coated at a spray rate of 97-101 kg/h and an air pressure of 1.7 bar with the coating solution as prepared above until the desired film-thickness of the coating had been reached. The product temperature of the pancreatin micropellet cores was monitored and maintained in the range between about 37° C. and about 43° C. during coating. The resulting pancreatin micropellets were then dried in a commercially available vacuum dryer (Vötsch type) at a temperature in a range between 35° C. and 50° C. for 12 hours. The dried pancreatin micropellets were then graded, first with a 0.7 mm sieve (sieving of undersize grain <0.7 mm) and then with a 1.6 mm sieve (sieving of oversize grain >1.6 mm) to yield 6532 g of pancreatin micropellets having a pancreatin content of about 60% relative to the enteric-coated pancreatin micropellets. The bulk density of the pancreatin micropellets was about 0.69 g/ml.

Further pancreatin micropellets were prepared according to the procedure described above and different coatings were applied in a manner similar to the coating process set forth above to yield further CRPCs. The compositions of the further CRPCs and other compositions are set forth in Table 1 along with certain process parameters from their respective coating processes. Composition G can be produced according to processes as described in U.S. Pat. No. 5,378,462. Comparative composition H was prepared according to a process which includes dibutylphthalate used as a plasticizer in the coating. All batches have been produced in laboratory scale unless otherwise noted.

TABLE 1

Pancreatin containing compositions

| | Ingredients mg/capsule | A | B | C | D | 1 | 2 |
|---|---|---|---|---|---|---|---|
| Micropellet Cores | Pancreatin | 150.00 | 150.00 | 150.00 | 150.00 | 150.00 | 150.00 |
| | PEG 4000 | 37.50 | 37.50 | 37.50 | 37.50 | 37.50 | 37.50 |
| Enteric Coating (film) | HP 55 | 48.60 | 48.60 | 48.60 | 48.60 | 48.60 | 48.60 |
| | Dimethicone | 1.25 | 1.25 | 1.25 | 1.25 | 1.25 | 1.25 |
| | TEC | 0 | 0 | 3.0 | 4.10 | 5.00 | 0 |
| | CA | 0 | 0.40 | 0 | 0 | 0 | 1.00 |
| | Sum | 237.40 | 237.75 | 240.35 | 241.45 | 242.4 | 238.35 |
| Process parameters | Pellet temp. while coating | 40° C. | 40° C. | 40° C. | 40° C. | 40° C. | 40° C. |

| | Ingredients mg/capsule | 3 | 4 | 5 | 6* | 7 | 8 |
|---|---|---|---|---|---|---|---|
| Micropellet Cores | Pancreatin | 150.00 | 150.00 | 150.00 | 150.00 | 150.00 | 150.00 |
| | PEG 4000 | 37.50 | 37.50 | 37.50 | 37.50 | 37.50 | 37.50 |
| Enteric Coating (film) | HP 55 | 52.60 | 48.60 | 48.60 | 52.25 | 52.25 | 52.25 |
| | Dimethicone | 1.25 | 1.25 | 1.25 | 1.25 | 1.25 | 1.25 |
| | TEC | 0 | 3.60 | 3.00 | 2.90 | 2.90 | 2.90 |
| | CA | 1.15 | 0.40 | 1.00 | 1.10 | 1.10 | 1.10 |
| | Sum | 242.50 | 241.35 | 241.35 | 245.00 | 245.00 | 245.00 |
| Process parameters | Pellet temp. while coating | 40° C. | 40° C. | 40° C. | 40° C. | 30° C. | 35° C. |

| | Ingredients mg/capsule | 9 | 10 | 11 | 12 | 13 | 14 |
|---|---|---|---|---|---|---|---|
| Micropellet | Pancreatin | 150.00 | 150.00 | 150.00 | 150.00 | 150.00 | 150.00 |
| | PEG 4000 | 37.50 | 37.50 | 37.50 | 37.50 | 37.50 | 37.50 |

TABLE 1-continued

Pancreatin containing compositions

| | | | | | | | |
|---|---|---|---|---|---|---|---|
| Enteric Coating (film) | HP 55 | 56.34 | 56.34 | 56.34 | 52.25 | 52.25 | 56.34 |
| | Dimethicone | 1.35 | 1.35 | 1.35 | 1.25 | 1.25 | 1.35 |
| | TEC | 3.13 | 3.13 | 3.13 | 2.90 | 2.90 | 3.13 |
| | CA | 1.19 | 1.19 | 1.19 | 1.10 | 1.10 | 1.19 |
| | Sum | 249.51 | 249.51 | 249.51 | 245.00 | 245.00 | 249.51 |
| Process parameters | Pellet temp. while coating | 37° C. | 40° C. | 43° C. | 49° C. | 40° C. | 46° C. |

| | | Composition | | | | |
|---|---|---|---|---|---|---|
| Ingredients mg/capsule | | 15 | E | F | G | H |
| Micropellet Cores | Pancreatin | 128.06 | 150.00 | 150.00 | 150.00 | 150.00 |
| | PEG 4000 | 32.01 | 37.50 | 37.50 | 37.50 | 37.50 |
| | Light mineral oil | 0 | 0 | 0 | 3.75 | 0 |
| Enteric Coating (film) | HP 55 | 48.10 | 48.60 | 48.60 | 48.60 | 48.60 |
| | Dimethicone | 1.15 | 1.25 | 1.25 | 1.25 | 1.25 |
| | TEC | 2.67 | 1.00 | 2.00 | 0 | 0 |
| | CA | 1.01 | 0 | 0 | 0 | 0 |
| | DBP | 0 | 0 | 0 | 4.10 | 4.10 |
| | Light mineral oil | 0 | 0 | 0 | 3.30 | 0 |
| | Sum | 213.00 | 238.35 | 239.35 | 248.50 | 241.50 |
| Process parameters | Pellet temp. while coating | n.a. | 40° C. | 40° C. | 40° C. | 40° C. |

Table 1 (continued);
PEG = polyethylene glycol; TEC = triethyl citrate; CA = cetyl alcohol; HP 55 = hydroxypropyl methylcellulose phthalate; temp. = temperature; DBP = dibutyl phthalate; *= production scale; n.a: data not available.

Compositions A, B, C, D, E, F, G and H are comparative compositions.

Composition G is a currently available high-quality pharmaceutical composition comprising pancreatin and light mineral oil.

Compositions No. 6, 10, 13, 14 and 15 are examples of compositions containing CA/TEC as the plasticizer.

Composition No. 3 is an example of a composition comprising cetyl alcohol as the plasticizer.

B. Determination of the Gastric Acid Resistance of Enteric Coated Pancreatin Micropellets at pH 1 and pH 5

The resistance to gastric acid of the pancreatin micropellets of Table 1.

Resistance to gastric juice (pH 1) of the different pancreatin micropellets from Table 1 was determined by immersing the micropellets for 2 hours in 0.1 mol/l hydrochloric acid in a disintegration tester according to the European Pharmacopoeia (Ph. Eur.). Then the un-dissolved portion of the pellets was separated from the solution and their residual lipase activity was determined according to the lipase assay of Ph. Eur./The International Pharmaceutical Federation" (FIP), PO Box 84200; 2508 AE The Hague; The Netherlands. The results of these tests for gastric resistance of the enteric coating are presented in Table 2 ("stability at pH 1").

Further, a similar test at pH 5 was performed using the same conditions as outlined above, with the exception that a phosphate buffer pH 5.0 (2.0 g sodium chloride and 9.2 g sodium di-hydrogen phosphate monohydrate per liter adjusted to pH 5.0) was used as a solvent instead of 0.1 mol/l hydrochloric acid. The results of these tests for gastric resistance are also presented below in Table 2 ("stability at pH 5").

The gastic acid resistances of the compositions from Table 1 (see above) are each given in Table 2 as percentages of the residual lipolytic activity after the incubation in relation to the actual lipolytic activity of the samples tested prior to the incubation (relative gastric acid resistance). The lipolytic activity is determined according to the lipase assay described in the USP monograph "pancrelipase delayed-release capsules". In principle, any standardized and characterized pancreatin sample may be used as the lipase reference standard. For example, a predetermined lipolytic activity standard may be obtained from the "International Pharmaceutical Federation" (FIP), PO Box 84200; 2508 AE The Hague; The Netherlands. For the purposes of the present invention, an internal pancreatin standard was used which is available on request from Solvay Pharmaceuticals GmbH, Hans-Boeckler-Allee 20, 30173 Hannover, Germany.

TABLE 2

Relative gastric acid resistances (stabilities) of compositions in Table 1 at pH 1 and pH 5

| Composition | Stability at pH 5 [%] | Stability at pH 1 [%] |
|---|---|---|
| A | 15.3 | 15.9 |
| B | 63.2 | 53.8 |
| C | 71.6 | 84.2 |
| D | 52.0 | 93.6 |
| 1 | 87.0 | 96.0 |
| 2 | 76.4 | 92.6 |
| 3 | 92.1 | 94.5 |
| 4 | 85.3 | 93.7 |
| 5 | 92.0 | 93.0 |
| 6 | 94.9 | 99.4 |
| 7 | 67.4 | 89.8 |
| 8 | 80.5 | 95.2 |
| 9 | 83.8 | 90.8 |
| 10 | 97.9 | 99.6 |
| 11 | 89.0 | 93.5 |
| 12 | 83.7 | 94.8 |
| 13 | 100.2 | 102.7 |
| 14 | 93.6 | 98.7 |
| E | 48.6 | 65.0 |
| F | 36.5 | 75.0 |
| G | 98.6 | 100.6 |

Preferred CRPCs have a gastric acid resistance (stability) at pH 1 of at least 75%, in particular of at least 85%, preferably of at least 90%, more preferred of at least 95%, relative to a predetermined pancreatin lipolytic activity standard.

Other preferred CRPCs as disclosed herein have a gastric acid resistance at pH 5 of at least 75%, in particular of at least 85%, preferably of at least 90%, more preferred of at least 95%, relative to a predetermined pancreatin lipolytic activity standard.

CRPCs which are most preferred have a gastric acid resistance at pH 1 of at least 90% and an additional gastric acid resistance at pH 5 of at least 90%, relative to a predetermined pancreatin lipolytic activity standard.

C. Determination of the Dissolution Profile of Enteric Coated Pancreatin Micropellets The dissolution profile of different compositions from Table 1 (see above) was determined according to a test procedure as described in the United States Pharmacopoeia (USP) monograph "pancrelipase delayed-release capsules" with increased gastric resistance phase which is hereby incorporated by reference.

The determination of the resistance to gastric fluid was performed using gastric juice without enzymes according to USP under standardized conditions (37° C., 100 rpm) for 2 hours in the dissolution apparatus (basket apparatus USP). Then the un-dissolved portion of the enteric coated pancreatin micropellets was separated from the solution and transferred into the paddle apparatus according to USP, filled with phosphate buffer solution at pH 6.0 to determine the dissolution of enzymes. The enteric coated pancreatin micropellets were agitated in a dissolution tester under standardized conditions for usually 90 minutes (see exact timepoints in Table 3 below) at 37° C. and 50 rpm.

The lipase activity was determined after selected time points (see Table 3) according to the lipase assay described in the USP monograph "pancrelipase delayed-release capsules".

Further, a test similar to that described above was performed with a "McIlvain buffer" (pH 6.0; for preparation mix solution A: 7.098 g $Na_2HPO_4$ anhydrous and 4 g of bile salts in 1000 ml water with solution B: 5.25 g $C_6H_8O_7.H_2O$ and 4 g of bile salts in 100 ml water) instead of a USP-compliant phosphate buffer. All other conditions remained as described above for the USP-compliant phosphate buffer.

The results of the dissolution profile tests are presented below as "% residual lipase activity of actual lipase activity" for the test series performed with USP-compliant phosphate buffer (see Table 3a) and for the test series performed with McIlvain buffer (see Table 3b).

TABLE 3a

Dissolution profiles of the enteric coated pancreatin micropellets in phosphate buffer

| Time points | % lipase activity of initial actual activity for each composition No. | | | | | |
|---|---|---|---|---|---|---|
| [min.] | G | 2 | 3 | 4 | 5 | 13 | 14 |
| 5 | 0.0 | — | 3.0 | — | 0.0 | 4.6 | NA |
| 10 | 0.0 | — | 4.9 | — | 6.2 | 4.6 | 15.37 |
| 15 | 11.9 | — | 16.4 | — | 37.8 | 17.6 | 34.38 |
| 20 | 48.0 | — | 39.3 | — | 63.5 | 40.8 | NA |
| 25 | 62.3 | — | 59.0 | — | 72.4 | 59.8 | NA |
| 30 | 73.5 | — | 67.8 | — | 80.0 | 66.2 | 73.86 |
| 45 | 77.1 | — | 80.5 | — | 84.0 | 76.6 | 84.45 |
| 60 | 79.9 | — | 77.8 | — | 84.2 | 81.9 | 81.25 |
| 75 | 78.4 | — | 77.1 | — | 78.9 | 79.8 | 80.40 |
| 90 | 78.2 | — | 72.3 | — | 77.2 | 77.4 | NA |

TABLE 3b

Dissolution profiles of the enteric coated pancreatin micropellet in McIlvain buffer

| Time points | % lipase activity of initial actual activity for each composition No. | | | | | |
|---|---|---|---|---|---|---|
| [min.] | G | 2 | 3 | 4 | 5 | 13 |
| 5 | 0.0 | 1.0 | 0.5 | 0.4 | 0.0 | 0.7 |
| 10 | 0.5 | 8.8 | 1.7 | 7.7 | 4.5 | 1.2 |
| 15 | 6.3 | 39.6 | 9.8 | 39.1 | 30.2 | 8.1 |
| 20 | 23.6 | 60.5 | 24.3 | 62.7 | 65.6 | 24.6 |
| 25 | 47.2 | 68.7 | 40.6 | 79.6 | 79.3 | 43.1 |
| 30 | 66.3 | 75.2 | 58.3 | 84.7 | 85.2 | 58.9 |
| 45 | 88.1 | 76.9 | 75.4 | 86.3 | 87.5 | 83.7 |
| 60 | 91.0 | 74.0 | 80.9 | 84.5 | 85.4 | 87.1 |
| 75 | 88.4 | 73.9 | 81.4 | 80.2 | — | 87.1 |
| 90 | — | 71.2 | 80.6 | — | — | 85.4 |
| 105 | — | — | 77.7 | — | — | — |

For the dissolution profile test results as provided in Tables 3a and 3b, a comparison of the compositions nos. 2, 3, 4, 5 and 13 was performed in each case with the reference composition "G". The comparison was based on the "Guidance for Industry", SU-PAC-MR, Modified Release Solid Oral Dosage Forms (September 1997), which is hereby incorporated by reference, by calculating the similarity factor (f2). The two acceptance limits for determining similarity of two compared curves were (i) a factor (f2)>50 and (ii) the average deviation at any dissolution sampling point should not be greater than 15%.

In vitro dissolution profile comparisons can be made using a model independent approach using similarity factor. Dissolution profiles may be compared using the following equation that defines a similarity factor ($f_2$):

$$f_2 = 50 \log \{[1+1/n\Sigma^n_{t=1}(R_t-T_t)^2]^{-0.5} * 100\}$$

where log=logarithm to base 10, n=number of sampling time points, $\Sigma$=summation over all time points, $R_t$=dissolution at time point t of the reference (unchanged drug product, i.e. prechange batch), $T_t$=dissolution at time point t of the test (changed drug product, i.e., post-change batch).

For comparison of multipoint dissolutionprofiles obtained in multiple media, similarity testing should be preformed using pairwise dissolution profiles (i.e., for the changed and unchanged product) obtained in each individual medium. An $f_2$ value between 50 and 100 suggests the dissolution profiles are similar.

When applying the above-stated acceptance limits for determining similarity it was found that the dissolution profiles of pancreatin micropellet CRPCs no. 2, 4 and 5 (see Table 1) could not be considered to be similar to the dissolution profile of the reference pancreatin micropellet "G" (see Table 1). However, when applying the above-stated acceptance limits for determining similarity it was found that the dissolution profiles of pancreatin micropellet CRPCs no. 3 and 13 (see Table 1) could be considered to be similar to the dissolution profile of the reference pancreatin micropellet "G" (see Table 1). Thus, pharmaceutical compositions containing pancreatin and their methods of manufacturing which are similar to composition G in Table 1 are specifically described herein.

D. Storage Stability Studies for Enteric Coated Pancreatin Micropellet CPRCs

For determining storage stability of different pancreatin micropellets from Table 1 (see above), hard gelatin capsules of size 0 were filled with approximately 497 mg of pancreatin micropellets (see Table 1) and packed into 30 ml HDPE bottles for performing the following tests.

The packed pancreatin micropellets were stored for 5 months under normal or two different aggravated storage conditions (see below for details) and the residual lipase activity was determined in each case analogously to the instructions of Ph. Eur. The results of these storage stability tests of the CPRCs after 5 months' storage periods are presented below in Tables 4a and 4b, respectively ("Lipase").

Resistance to gastric juice (pH 1) of the different pancreatin micropellets from Table 1 was also determined after a total storage period of 5 months by immersing pancrelipase delayed-release pellets for 2 hours in 0.1 mol/l hydrochloric acid in a disintegration tester according to the Ph. Eur. (Section 2.9.1. "disintegration"). The un-dissolved portion of the pellets was then separated from the solution and their residual lipase activity was determined according to the lipase assay of Ph. Eur. (monograph "pancreas powder"). The results of these tests for gastric resistance of the enteric coating after 5 months' storage periods under normal or two different aggravated storage conditions are presented in Tables 4a and 4b, respectively ("gastric resistance at pH 1").

Further, a similar test at pH 5 was done using the same conditions as outlined in the previous paragraph, with the exception that a phosphate buffer pH 5.0 (2.0 g sodium chloride and 9.2 g sodium di-hydrogen phosphate monohydrate per liter adjusted to pH 5.0) was used as a solvent instead of 0.1 mol/l hydrochloric acid. The results of these tests for gastric resistance of the enteric coating after 5 months' storage periods are presented below in Tables 4a and 4b, respectively ("gastric resistance at pH 5").

TABLE 4a

Stability results for select compositions from Table 1 at 30° C. and 65% rel. humidity (slightly aggravated storage conditions)

| | | % lipase activity of initial activity | |
|---|---|---|---|
| | CPRC | Months | |
| Conditions | No. | 0 | 5 |
| Lipase (initial activity) | G | 100 | 92 |
| | 3 | 100 | 88 |
| | 13 | 100 | 94 |
| Gastric resistance at pH 1 (actual activity) | G | 101 | 91 |
| | 3 | 95 | 95 |
| | 13 | 103 | 99 |
| Gastric resistance at pH 5 (actual activity) | G | 99 | 92 |
| | 3 | 92 | 86 |
| | 13 | 100 | 95 |

TABLE 4b

Stability results for select compositions from Table 1 at 40° C. and 75% rel. humidity (aggravated storage conditions)

| | CPRC | % lipase activity of initial activity Months | | | | | |
|---|---|---|---|---|---|---|---|
| Conditions | No. | 0 | 1 | 2 | 3 | 4 | 5 |
| Lipase (initial activity) | G | 100 | 90 | 80 | 77 | 69 | 64 |
| | 3 | 100 | 87 | 79 | 69 | 64 | 61 |
| | 13 | 100 | 97 | 87 | 81 | 73 | 67 |
| Gastric resistance at pH 1 (actual activity) | G | 101 | 96 | 101 | 94 | 96 | 96 |
| | 3 | 95 | 94 | 94 | 96 | 87 | 86 |
| | 13 | 103 | 95 | 97 | 97 | 96 | 89 |
| Gastric resistance at pH 5 (actual activity) | G | 99 | 92 | 95 | 76 | 87 | 40 |
| | 3 | 92 | 86 | 78 | 63 | 51 | 22 |
| | 13 | 100 | 90 | 83 | 73 | 43 | 15 |

The data presented in Tables 4a and 4b illustrate that the tested composition Nos. G, 3 and 13 (see Table 1) are of satisfactory storage stability under normal and slightly aggravated storage conditions over a 5 months storage period. The lipase content of composition No. 13, although similar to the two comparative compositions, was best preserved over the observed 5 months' periods under slightly aggravated and aggravated storage conditions.

Under slightly aggravated storage conditions, which are most relevant in practice, composition No. 13 performed best in terms of gastric resistance at pH 1 and pH 5 over the observed 5 months' periods.

All references, including publications, patent applications, and patents, cited herein are hereby incorporated by reference to the same extent as if each reference there individually and specifically indicated to be incorporated by reference were set forth in its entirety herein.

In the present disclosure, where numeric values are given as ranges, the respective range limits are generally meant to be included in and being part of the given ranges unless expressly stated otherwise.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the invention.

Alternative embodiments of the claimed invention are described herein, including the best mode known to the inventors for carrying out the claimed invention. Of these, variations of the disclosed embodiments will become apparent to those of ordinary skill in the art upon reading the foregoing disclosure. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately" unless clearly indicated by context otherwise. Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the claimed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately". Thus, recitation of ranges of values herein are merely intended to serve as a shorthand method of referring individually to each and every separate value falling within the range, unless otherwise indicated herein, and each separate value is incorporated into the specification as if it were individually recited herein.

We claim:

1. A process for the manufacture of pancreatin micropellets, comprising the steps of:
   a. providing pancreatin micropellet cores which comprises pancreatin and at least one pharmaceutically acceptable binding agent, wherein the binding agent is selected from the group consisting of: polyethylene glycol 2000, polyethylene glycol 3000, polyethylene glycol 4000, polyethylene glycol 6000, polyethylene glycol 8000 and polyethylene glycol 10000, wherein the pancreatin micropellet cores are substantially free of synthetic oils;
   b. providing an enteric coating solution comprising
      i. one or more film forming agents, wherein said one or more film forming agents are selected from the group consisting of: hydroxypropyl cellulose, hydroxypropylmethyl acetate succinate, hydroxypropyl methyl cellulose acetate succinate, hydroxypropyl methylcellulose phthalate, and methyl cellulose;
      ii. a plasticizer comprising cetyl alcohol and triethyl citrate which are collectively present in an amount greater than about 3% by weight relative to the one or more film forming agents and wherein the weight to weight ratio of cetyl alcohol to triethyl citrate is from about 0.38:1 to about 0.4:1 and wherein the plasticizer is substantially free of monomeric phthalic acid esters; and
      iii. optionally, at least one anti-sticking agent, and
      iv. one or more enzyme-friendly organic solvent(s);
   c. coating the pancreatin micropellet cores with the enteric coating solution wherein the temperature of the pancreatin micropellet cores during coating is kept at a temperature suitable to apply the enteric coating solution; and
   d. drying the enteric-coated pancreatin micropellet cores.

2. The process of claim 1 wherein the enteric coating is between about 20% and about 30% by weight of the pancreatin micropellets.

3. The process of claim 1 wherein the cetyl alcohol and triethyl citrate are collectively present in an amount between about 4% and about 20% by weight relative to the film forming agent.

4. The process of claim 1 wherein the anti-sticking agent is selected from the group consisting of: dimethicone and castor oil.

5. The process of claim 1 wherein the anti-sticking agent is present in an amount between about 1.5% and about 3% by weight relative to the film forming agent.

6. The process of claim 1 wherein the one or more enzyme-friendly organic solvents is selected from the group consisting of: acetone, chloroform, dichloromethane, methanol, ethanol, 1-propanol, 2-propanol, 2-butanol, tert-butanol and mixtures of said solvents.

7. A method of treating a medical condition in a mammalian subject, comprising the steps of:
   a. providing pancreatin micropellets resulting from the process of claim 1 in a dosage form suitable for oral administration; and
   b. orally administering the dosage form to the subject to provide pancreatin in an amount sufficient to treat the medical condition; wherein the medical condition is selected from the group consisting of: pancreatic exocrine insufficiency, pancreatitis, cystic fibrosis, diabetes type I and diabetes type II.

8. A pharmaceutical composition, comprising
   a. a pharmacologically effective amount of pancreatin wherein said pancreatin is in the form of pancreatin micropellets resulting from the process of claim 1; and
   b. a dosage form suitable for oral administration containing said pharmacologically effective amount of pancreatin.

9. A pharmaceutical composition prepared by a process comprising the steps of:
   a. preparing an extrudable mixture comprising:
      i. about 10% to about 95% pancreatin;
      ii. about 5% to about 90% of at least one pharmaceutically acceptable binding agent, wherein the binding agent is selected from the group consisting of: polyethylene glycol 2000, polyethylene glycol 3000, polyethylene glycol 4000, polyethylene glycol 6000, polyethylene glycol 8000 and polyethylene glycol 10000, wherein the pancreatin micropellet cores are substantially free of synthetic oils;
      iii. 0% to about 10% of at least one pharmaceutically acceptable excipient; and
      iv. one or more enzyme-friendly organic solvents in an amount sufficient to form an extrudable mixture; wherein the percentages of components are weight to weight of the extrudable mixture;
   b. creating pancreatin micropellet cores from the extrudable mixture;
   c. forming the pancreatin micropellet cores into approximately spherical or approximately ellipsoidal shape in the presence of additional enzyme-friendly organic solvent;
   d. removing the one or more enzyme-friendly organic solvents from the pancreatin micropellet cores such that the pancreatin micropellet cores are substantially free of the one or more enzyme-friendly organic solvents;
   e. coating the pancreatin micropellet cores with an enteric coating solution comprising:
      i. one or more film forming agents, wherein said one or more film forming agents are selected from the group consisting of: hydroxypropyl cellulose, hydroxypropylmethyl acetate succinate, hydroxypropyl methyl cellulose acetate succinate, hydroxypropyl methylcellulose phthalate and methyl cellulose;
      ii. a plasticizer comprising cetyl alcohol and triethyl citrate which are collectively present in an amount greater than about 3% by weight relative to the one or more film forming agents and wherein the weight to weight ratio of cetyl alcohol to triethyl citrate is from about 0.38:1 to about 0.4:1; and
      iii. optionally at least one anti-sticking agent in one or more enzyme-friendly organic solvent;

wherein the temperature of the pancreatin micropellet cores during coating is kept at a temperature suitable to apply the enteric coating solution and wherein the enteric coating solution is substantially free of monomeric phthalic acid esters;

f. drying the enteric-coated pancreatin micropellet cores; and g. placing the enteric-coated pancreatin micropellet cores in a dosage form suitable for oral administration.

10. The pharmaceutical composition prepared by the process of claim 9 wherein the pancreatin is present between about 70% and about 90% weight to weight of the pancreatin micropellet cores.

11. The pharmaceutical composition prepared by the process of claim 9, wherein the binding agent is present between about 10% and about 30% weight to weight of the pancreatin micropellet cores.

12. The pharmaceutical composition prepared by the process of claim 9, wherein the binding agent is polyethylene glycol 4000.

13. The pharmaceutical composition prepared by the process of claim 9, wherein the at least one pharmaceutically acceptable excipient is selected from the group consisting of: magnesium stearate, calcium stearate, stearic acid, talcum, starch, calcium phosphate, corn starch, dextrans, dextrin, hydrated silicon dioxide, microcrystalline cellulose, kaolin, lactose, mannitol, polyvinyl pyrrolidone, precipitated calcium carbonate, sorbitol, silicic acid, alginic acid, amylose, calcium alginate, calcium carbonate, formaldehyde gelatin, pectic carbonate, sago starch, sodium bicarbonate and glycerol.

14. The pharmaceutical composition prepared by the process of claim 9, wherein the one or more enzyme-friendly organic solvents are present between about 15% and about 35% by weight relative to the amount of pancreatin.

15. The pharmaceutical composition prepared by the process of claim 9, wherein the one or more enzyme-friendly organic solvents is selected from the group consisting of: acetone, chloroform, dichloromethane, methanol, ethanol, 1-propanol, 2-propanol, 2-butanol, tert-butanol and mixtures of said solvents.

16. The pharmaceutical composition prepared by the process of claim 9, wherein the one or more enzyme-friendly organic solvents is 2-propanol.

17. The pharmaceutical composition prepared by the process of claim 9, wherein removing the one or more enzyme-friendly organic solvents from the pancreatin micropellet cores is by drying at a temperature between about 30° C. and about 75° C.

18. A pharmaceutical composition prepared by a process comprising the steps of:
a. providing pancreatin micropellet cores which comprise at least one pharmaceutically acceptable binding agent, wherein the binding agent is selected from the group consisting of: polyethylene glycol 2000, polyethylene glycol 3000, polyethylene glycol 4000, polyethylene glycol 6000, polyethylene glycol 8000 and polyethylene glycol 10000, wherein the pancreatin micropellet cores are substantially free of synthetic oils;
b. providing an enteric coating solution comprising
   i. at least one film forming agent, wherein said film forming agent is selected from the group consisting of: hydroxypropyl cellulose, hydroxypropylmethyl acetate succinate, hydroxypropyl methyl cellulose acetate succinate, hydroxypropyl methylcellulose phthalate and methyl cellulose;
   ii. a plasticizer comprising cetyl alcohol and triethyl citrate which are collectively present in an amount of greater than about 3% by weight relative to the one or more film forming agents and wherein the weight to weight ratio of cetyl alcohol to triethyl citrate is from about 0.38:1 to about 0.4:1 and wherein the plasticizer is substantially free of monomeric phthalic acid esters; and
   iii. optionally at least one anti-sticking agent in one or more enzyme-friendly organic solvent;
c. coating the pancreatin micropellet cores with the enteric coating solution wherein the temperature of the pancreatin micropellet cores during coating is kept at a temperature suitable to apply the enteric coating solution;
d. drying the enteric-coated pancreatin micropellet cores; and
e. placing the enteric-coated pancreatin micropellet cores in a dosage form suitable for oral administration.

19. The composition of claim 18 wherein the enteric coating is between about 20% and about 30% by weight of the pancreatin micropellets.

20. The composition of claim 18 wherein the anti-sticking agent is selected from the group consisting of: dimethicone and castor oil.

21. The composition of claim 18 wherein the anti-sticking agent is present in an amount between about 1.5% and about 3% by weight relative to the film forming agent.

22. The composition of claim 18 wherein the one or more enzyme-friendly organic solvents is selected from the group consisting of: acetone, chloroform, dichloromethane, methanol, ethanol, 1-propanol, 2-propanol, 2-butanol, tert-butanol and mixtures of said solvents.

23. The pharmaceutical composition of claim 18, wherein the enteric-coated pancreatin micropellets have a gastric acid resistance of about 75% or more at about pH 1.

24. The pharmaceutical composition of claim 18, wherein the enteric-coated pancreatin micropellets have a gastric acid resistance of about 75% or more at about pH 5.

25. A pharmaceutical composition comprising:
a. pancreatin micropellet cores which comprise at least one pharmaceutically acceptable binding agent, wherein the binding agent is selected from the group consisting of: polyethylene glycol 2000, polyethylene glycol 3000, polyethylene glycol 4000, polyethylene glycol 6000, polyethylene glycol 8000 and polyethylene glycol 10000, wherein the pancreatin micropellet cores are substantially free of synthetic oils;
b. at least one film forming agent, wherein said film forming agent is selected from the group consisting of: hydroxypropyl cellulose, hydroxypropylmethyl acetate succinate, hydroxypropyl methyl cellulose acetate succinate, hydroxypropyl methylcellulose phthalate and methyl cellulose;
c. a plasticizer comprising cetyl alcohol and triethyl citrate which are collectively present in an amount greater than about 3% by weight relative to the one or more film forming agents and wherein the weight to weight ratio of cetyl alcohol to triethyl citrate is from about 0.38:1 to about 0.4:1 and wherein the plasticizer is substantially free of monomeric phthalic acid esters; and
d. optionally at least one anti-sticking agent.

26. The pharmaceutical composition of claim 25, wherein the percent lipase activity present in a phosphate buffer solution is greater than 0% after 10 minutes, greater than about 30% after 20 minutes, greater than about 50% after 30 minutes and greater than about 65% after 60 minutes as measured according to the United States Pharmacopoeia using a phosphate buffer solution at pH 6.

27. The pharmaceutical composition of claim 25, wherein the percent lipase activity present in a phosphate buffer solution is greater than 0.1% after 10 minutes, greater than about 15% after 20 minutes, greater than about 45% after 30 minutes and greater than about 65% after 60 minutes as measured according to the United States Pharmacopoeia but using a McIlvaine's (citrate-phosphate) buffer solution at pH 6.

28. The pharmaceutical composition of claim 25, wherein the percent lipase activity is greater than about 75% after five months in an environment of about 30° C. and about 65% relative humidity.

29. The pharmaceutical composition of claim 25, wherein the composition has a gastric acid resistance of about 75% or more at about pH 1 after five months in an environment of about 30° C. and about 65% relative humidity.

30. The pharmaceutical composition of claim 25, wherein the composition has a gastric acid resistance of about 75% or more at about pH 5 after five months in an environment of about 30° C. and about 65% relative humidity.

31. The pharmaceutical composition of claim 25, wherein the pharmaceutical composition has a dissolution profile with a similarity factor ($f_2$) greater than 50 when compared to the dissolution profile of composition G in Table 1;

wherein $f_2$ is determined by the formula:

$$f_2 = 50 \log \{[1+1/n\Sigma^n_{t=1}(R_t-T_t)^2]^{-0.5} * 100\}.$$

32. The pharmaceutical composition of claim 25, wherein the pharmaceutical composition has a dissolution profile with a similarity factor ($f_2$) greater than 50 when compared to the dissolution profile of composition 13 in Table 1;

wherein $f_2$ is determined by the formula:

$$f_2 = 50 \log \{[1+1/n\Sigma^n_{t=1}(R_t-T_t)^2]^{-0.5} * 100\}.$$

* * * * *